(12) United States Patent
Ema et al.

(10) Patent No.: US 7,991,108 B2
(45) Date of Patent: Aug. 2, 2011

(54) MEDICAL IMAGE PROCESSING APPARATUS, ULTRASOUND IMAGING APPARATUS, X-RAY CT (COMPUTED TOMOGRAPHY) APPARATUS, AND METHOD OF PROCESSING MEDICAL IMAGE

(75) Inventors: Takehiro Ema, Otawara (JP); Hitoshi Yamagata, Otawara (JP); Kota Aoyagi, Yaita (JP); Kyoko Sato, Nasushiobara (JP); Shunsuke Satoh, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/497,984

(22) Filed: Jul. 6, 2009

(65) Prior Publication Data
US 2010/0040200 A1    Feb. 18, 2010

(30) Foreign Application Priority Data
Aug. 18, 2008   (JP) .................. 2008-209664

(51) Int. Cl.
*A61B 6/02* (2006.01)
(52) U.S. Cl. .................. 378/41; 378/4; 378/8
(58) Field of Classification Search ............ 378/4, 41, 378/98.12
See application file for complete search history.

(56) References Cited

U.S. PATENT DOCUMENTS

| | | | | |
|---|---|---|---|---|
| 4,882,679 A * | 11/1989 | Tuy et al. | .................. | 600/425 |
| 4,947,347 A * | 8/1990 | Sato | .................. | 345/421 |
| 5,371,778 A * | 12/1994 | Yanof et al. | .................. | 378/4 |
| 5,493,595 A * | 2/1996 | Schoolman | .................. | 378/41 |
| 5,694,530 A * | 12/1997 | Goto | .................. | 345/419 |
| 5,734,384 A * | 3/1998 | Yanof et al. | .................. | 345/424 |
| 6,175,655 B1 * | 1/2001 | George et al. | .................. | 382/257 |
| 6,278,767 B1 * | 8/2001 | Hsieh | .................. | 378/163 |
| 6,426,987 B2 * | 7/2002 | Nakamura et al. | .................. | 378/4 |
| 6,487,432 B2 * | 11/2002 | Slack | .................. | 600/407 |
| 7,035,371 B2 * | 4/2006 | Boese et al. | .................. | 378/41 |
| 7,154,985 B2 * | 12/2006 | Dobbs et al. | .................. | 378/4 |
| 7,336,758 B2 * | 2/2008 | Seto et al. | .................. | 378/4 |
| 2003/0156746 A1 * | 8/2003 | Bissell et al. | .................. | 382/128 |
| 2005/0093861 A1 * | 5/2005 | Moreau-Gobard | .................. | 345/419 |
| 2006/0056690 A1 * | 3/2006 | Schoisswohl et al. | .................. | 382/173 |

FOREIGN PATENT DOCUMENTS
JP    7-320068    12/1995
(Continued)

*Primary Examiner* — Edward J Glick
*Assistant Examiner* — Alexander H Taningco
(74) *Attorney, Agent, or Firm* — Oblon, Spivak, McClelland, Maier & Neustadt, L.L.P.

(57) ABSTRACT

A cardiac cavity region specifying part specifies the position of a cardiac cavity region represented in volume data. An image generation plane determining part determines an image generation plane that includes a rotation axis intersecting the cardiac cavity region. With a direction orthogonal to the image generation plane as a view direction, a first image generator generates three-dimensional image data that three-dimensionally represents a region excluding the cardiac cavity region, based on data excluding data included in the cardiac cavity of the volume data. A second image generator generates two-dimensional image data that two-dimensionally represents a region in the image generation plane, based on the data excluding the data included in the cardiac cavity region of the volume data. An image synthesizer synthesizes the three-dimensional image data with the two-dimensional image data. A display controller causes a display to display the synthesized image.

20 Claims, 13 Drawing Sheets

FOREIGN PATENT DOCUMENTS

| | | |
|---|---|---|
| JP | 10-99328 | 4/1998 |
| JP | 2000-210289 | 8/2000 |
| JP | 2000-217818 | 8/2000 |
| JP | 2000-250804 | 9/2000 |
| JP | 2005-161032 | 6/2005 |

* cited by examiner

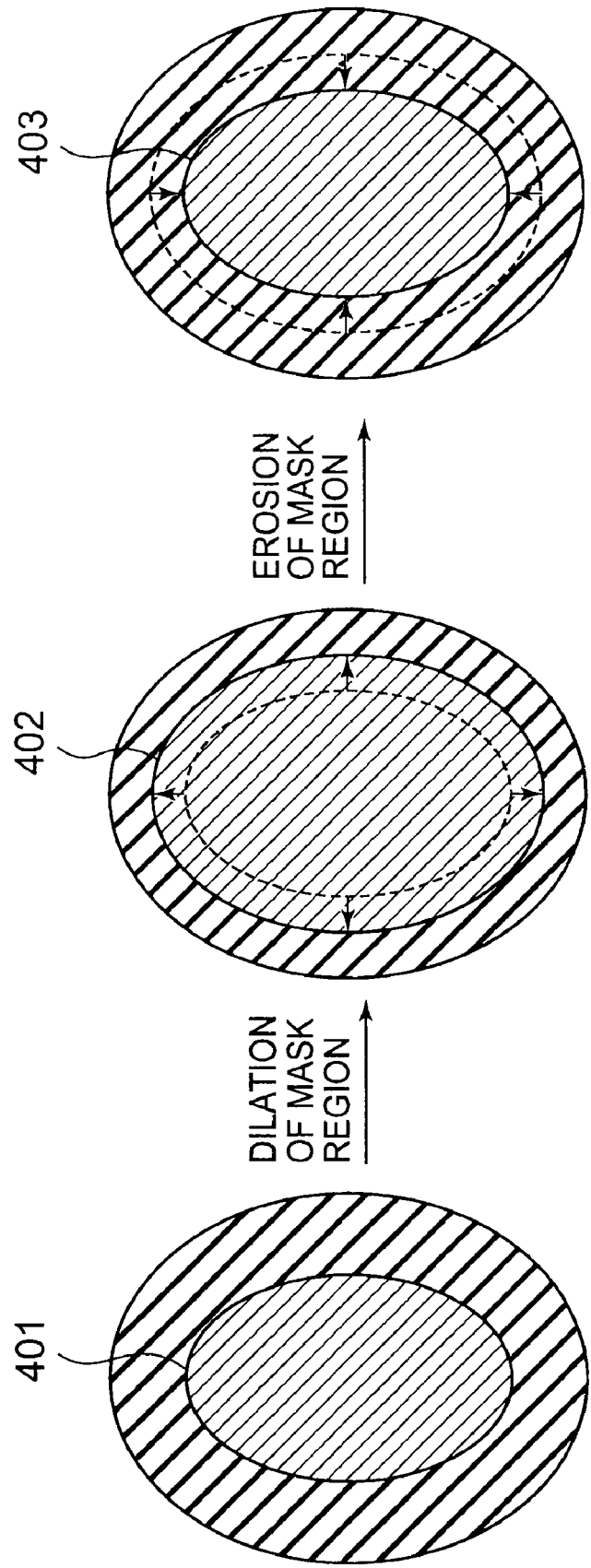

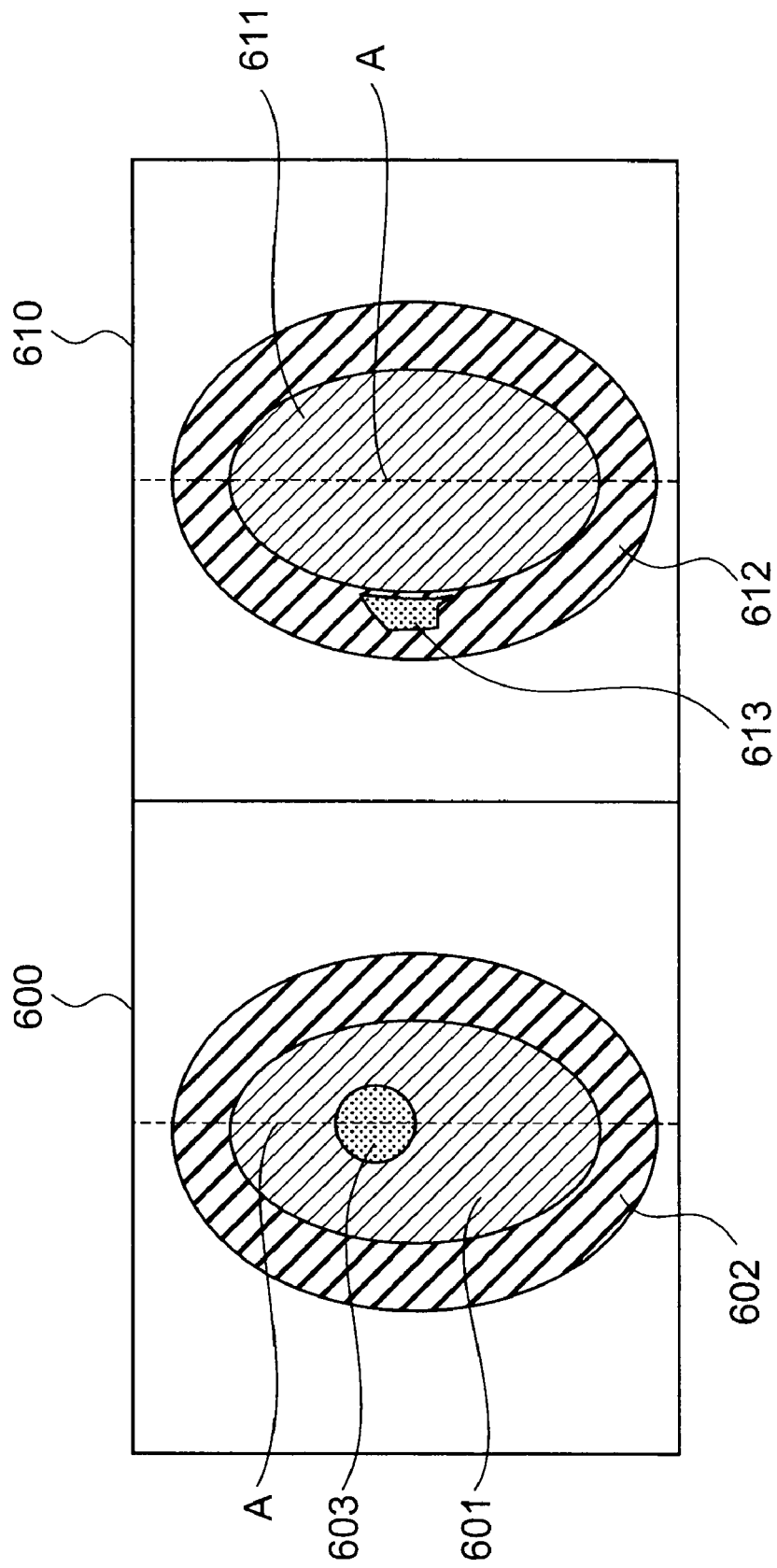

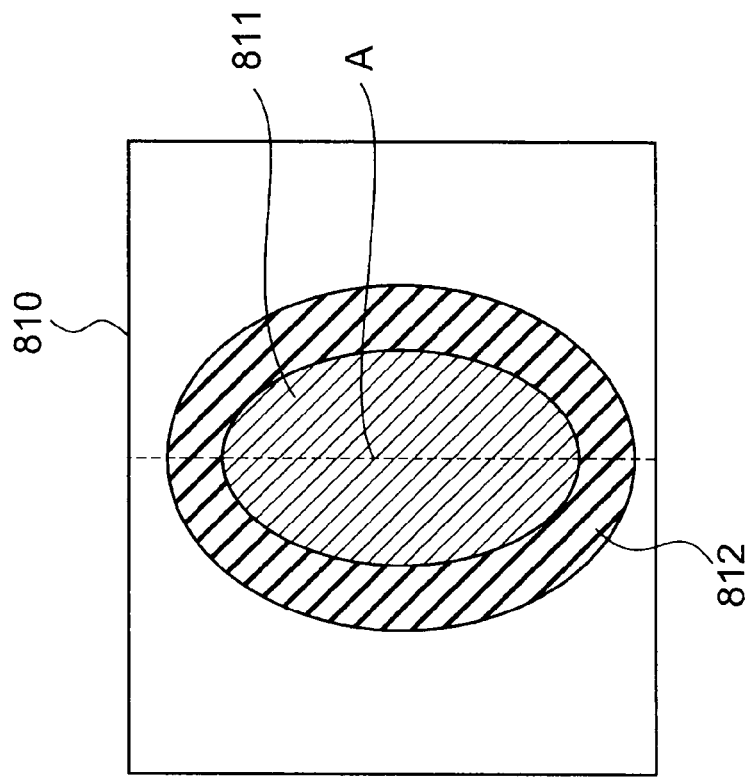
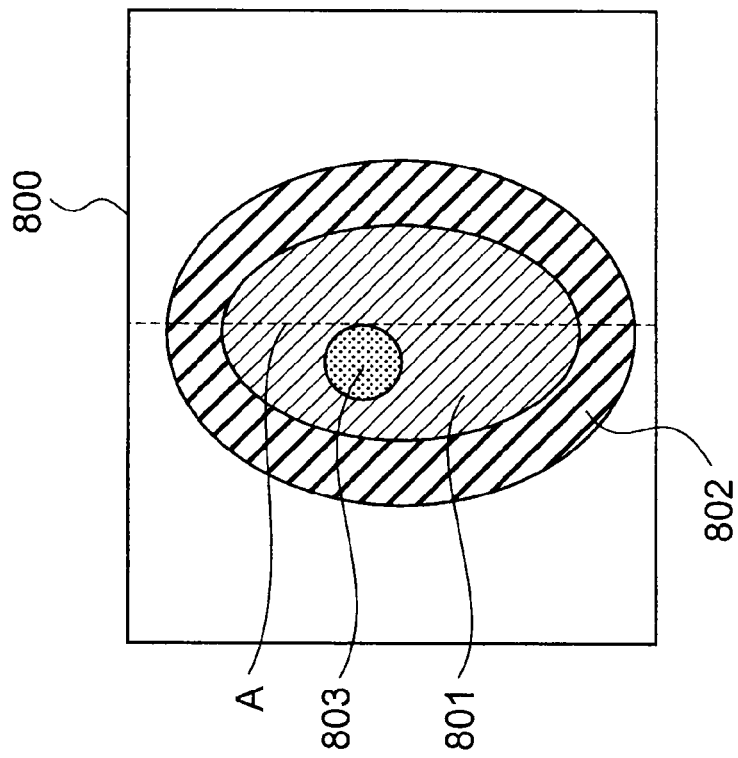
FIG. 11

MEDICAL IMAGE PROCESSING APPARATUS, ULTRASOUND IMAGING APPARATUS, X-RAY CT (COMPUTED TOMOGRAPHY) APPARATUS, AND METHOD OF PROCESSING MEDICAL IMAGE

BACKGROUND OF THE INVENTION

1. Field of the Invention

The present invention relates to a medical image processing apparatus, ultrasound imaging apparatus and X-ray CT apparatus, which generate image data suitable for diagnosis of a heart, and also relates to a method of processing a medical image.

2. Description of the Related Art

One of the important tasks in clinical diagnosis of a heart is advancement of a technique of assessing myocardial ischemia. In assessment of myocardial ischemia, an ultrasound imaging apparatus is used to capture an image by a method such as the color Doppler method and the contrast image method using a contrast medium. In this image capture, a state that the coronary artery or myocardium of the heart is deeply stained with the contrast medium is extracted as an ultrasound image such as a color Doppler image, a power Doppler image and a contrast image. Then, an ischemic part of the heart, which is a three-dimensional structure, is diagnosed by the extracted image.

An ultrasound imaging apparatus that is capable of acquiring volume data representing a three-dimensional region by scanning the inside of the three-dimensional region with ultrasound waves is known. By a three-dimensional ultrasound image such as a CFM (Color Flow Mapping) image, a power Doppler image and a three-dimensional contrast image generated by the ultrasound imaging apparatus, clinical diagnosis is conducted.

Further, an X-ray CT apparatus is provided with a multi detector and is thereby capable of generating image data of movement of a heart in real time. This enables observation of the movement of the heart as a three-dimensional moving image.

An ultrasound imaging apparatus for assessing myocardial ischemia by a three-dimensional image is known (e.g., Japanese Unexamined Patent Publication JP-A 2000-210289). This ultrasound imaging apparatus acquires volume data representing a heart by transmitting and receiving ultrasound waves. Then, the ultrasound imaging apparatus specifies a cardiac cavity region from the volume data and executes a mask process on data representing the inside of the cardiac cavity region. Then, the ultrasound imaging apparatus sets a division plane passing through the long axis of the heart, and divides, by the division plane, a region represented in the volume data subjected to the mask process into plural regions. By executing image processing such as the MIP (Maximum Intensity Projection) process on the divided volume data, the ultrasound imaging apparatus generates ultrasound image data such as MIP image data and displays an ultrasound image.

Moreover, in this conventional art, after the MIP process is executed in a direction to the endocardium, data is projected to a two-dimensional plane and the projected data is displayed.

Diagnosis of myocardial ischemia requires grasp of how ischemic portions of the myocardium are distributed from the inside to outside of the myocardium. However, it is difficult for an observer to grasp how the ischemic portions are distributed based on an ultrasound image generated by the ultrasound imaging apparatus of the conventional art. Even if, for example, an MIP image or a three-dimensional image generated by volume rendering is displayed, it is difficult for the observer to clearly grasp the distribution of the ischemic portions.

Further, since the MIP image is an image obtained by projecting volume data to a two-dimensional plane, it is hard to three-dimensionally see.

Although the MIP image is displayed while the volume data is rotated in the conventional art, it is difficult for the observer to grasp how the ischemic portions are distributed from the inside to outside of the myocardium.

Further, a three-dimensional image generated by volume rendering is generally subjected to the shadowing process so as to three-dimensionally show a subject represented in the image. Because of this shadowing process, the three-dimensional image does not clearly show shading represented in the original data, and therefore, it is difficult for the observer to read the shading from the three-dimensional image. Accordingly, it is difficult to grasp the distribution of the ischemic portions in the myocardium only by the three-dimensional image generated by volume rendering.

Thus, it is required to display so that the operator can easily grasp distribution of lesion sites, such as the distribution of the ischemic portions in the myocardium.

SUMMARY OF THE INVENTION

An object of the present invention is to provide a medical image processing apparatus, ultrasound imaging apparatus and X-ray CT apparatus, which are capable of generating medical image data that facilitate observation of a lesion part, and also provide a method of processing a medical image.

In a first aspect of the present invention, a medical image processing apparatus has: a cardiac cavity region specifying part configured to receive volume data representing a heart and specify a position of a cardiac cavity region represented in the volume data; an axis setting part configured to set an axis intersecting the cardiac cavity region; an image generation plane setting part configured to set an image generation plane including the axis in the volume data; a first image generator configured to, based on the volume data, generate three-dimensional image data that stereoscopically represents a boundary of the cardiac cavity region, which is a boundary of one of regions of the cardiac cavity region divided by the image generation plane; a second image generator configured to, based on data excluding data included in the cardiac cavity region of the volume data, generate two-dimensional image data that two-dimensionally represents a region in the image generation plane; and a display controller configured to generate synthesized image data by synthesizing the three-dimensional image data and the two-dimensional image data, and cause a display to display a synthesized image based on the synthesized image data.

According to the first aspect, a boundary of the cardiac cavity region, which is a boundary of one of regions of the cardiac cavity region divided by the image generation plane, is displayed with a three-dimensional image, and the tissue in the image generation plane excluding the cardiac cavity region is displayed with a two-dimensional image, whereby it is possible to stereoscopically display and observe the boundary of the cardiac cavity region and also observe a site around the cardiac cavity region with the two-dimensional image. Consequently, it is possible to display a lesion site existing in the site around the cardiac cavity region with the two-dimensional image or the three-dimensional image, depending on a position in which the image generation plane is set. For example, by displaying a lesion site in a two-dimensional image, the operator can observe the state of distribution of the lesion site in the image generation plane. Moreover, by displaying a lesion site in a three-dimensional image, it is possible to stereoscopically display and observe the lesion site. Thus, according to the first aspect, it is possible to display lesion sites distributed around a cardiac cavity region in an easily observable manner.

Further, in a second aspect of the present invention, an ultrasound imaging apparatus has: an imaging part configured to, with a heart of a subject as an imaging target, transmit ultrasound waves to the subject and acquire volume data representing the heart of the subject based on reflected waves from the subject; a cardiac cavity region specifying part configured to specify a position of a cardiac cavity region represented in the volume data; an axis setting part configured to set an axis intersecting the cardiac cavity region; an image generation plane setting part configured to set an image generation plane including the axis in the volume data; a first image generator configured to, based on the volume data, generate three-dimensional image data that stereoscopically represents a boundary of the cardiac cavity region, which is a boundary of one of regions of the cardiac cavity region divided by the image generation plane; a second image generator configured to generate two-dimensional image data that two-dimensionally represents a region in the image generation plane based on data excluding data included in the cardiac cavity region of the volume data; and a display controller configured to generate synthesized image data by synthesizing the three-dimensional image data and the two-dimensional image data, and cause a display to display a synthesized image based on the synthesized image data.

Further, in a third aspect of the present invention, an X-ray CT apparatus has: an imaging part configured to, with a heart of a subject as an imaging target, irradiate the subject with an X-ray and acquire volume data representing the heart of the subject based on the X-ray transmitted through the subject; a cardiac cavity region specifying part configured to specify a position of a cardiac cavity region represented in the volume data; an axis setting part configured to set an axis intersecting the cardiac cavity region; an image generation plane setting part configured to set an image generation plane including the axis in the volume data; a first image generator configured to, based on the volume data, generate three-dimensional image data that stereoscopically represents a boundary of the cardiac cavity region, which is a boundary of one of regions of the cardiac cavity region divided by the image generation plane; a second image generator configured to generate two-dimensional image data that two-dimensionally represents a region in the image generation plane based on data excluding data included in the cardiac cavity region of the volume data; and a display controller configured to generate synthesized image data by synthesizing the three-dimensional image data and the two-dimensional image data, and cause a display to display a synthesized image based on the synthesized image data.

Further, in a fourth aspect of the present invention, a method of processing a medical image includes: receiving volume data that represents a heart and specifying a position of a cardiac cavity region represented in the volume data; setting an axis that intersects the cardiac cavity region; setting an image generation plane that includes the axis in the volume data; generating three-dimensional image data that stereoscopically represents a boundary of the cardiac cavity region, which is a boundary of one of regions of the cardiac cavity region divided by the image generation plane, based on the volume data; generating two-dimensional image data that two-dimensionally represents a region in the image generation plane based on data excluding data included in the cardiac cavity region of the volume data; and generating synthesized image data by synthesizing the three-dimensional image data and the two-dimensional image data, and displaying a synthesized image based on the synthesized image data.

BRIEF DESCRIPTION OF THE DRAWINGS

FIG. 6 is a schematic view for describing the size of a mask region.

FIG. 8 is a view schematically showing an image generated by the medical image processing apparatus according to the embodiment of the present invention.

FIG. 11 is a view schematically showing an image generated by the medical image processing apparatus according to the embodiment of the present invention.

DETAILED DESCRIPTION OF THE EMBODIMENTS

Figure 1:
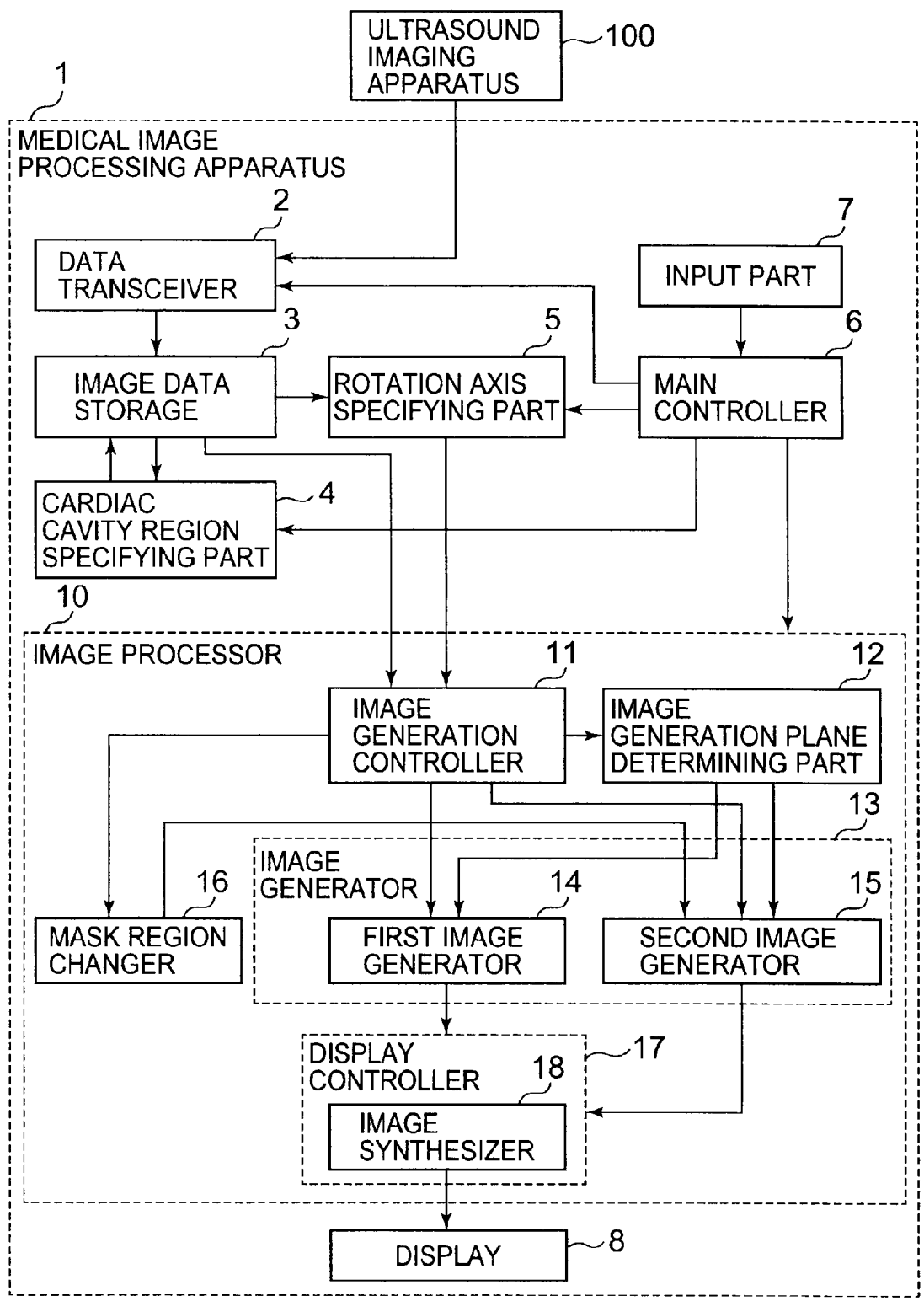
FIG. 1 is a block diagram showing a medical image processing apparatus according to an embodiment of the present invention.

A medical image processing apparatus according to an embodiment of the present invention will be described with reference to FIG. 1. FIG. 1 is a block diagram showing the medical image processing apparatus according to the embodiment of the present invention.

(Ultrasound Imaging Apparatus 100)

An ultrasound imaging apparatus 100 has an ultrasound probe. The ultrasound imaging apparatus 100 transmits ultrasound waves to a subject and receives reflected waves from the subject, thereby generating ultrasound image data based on the reflected waves. Moreover, the ultrasound imaging apparatus 100 attaches supplementary information including the patient name, examination ID and examination date to the ultrasound image data. The ultrasound image data acquired by the ultrasound imaging apparatus 100 is stored into an image storing apparatus, which is not shown. Moreover, a medical image processing apparatus 1 reads the ultrasound image data from the ultrasound imaging apparatus 100 or the image storing apparatus, and stores the read ultrasound image data into an image data storage 3.

Figure 2:
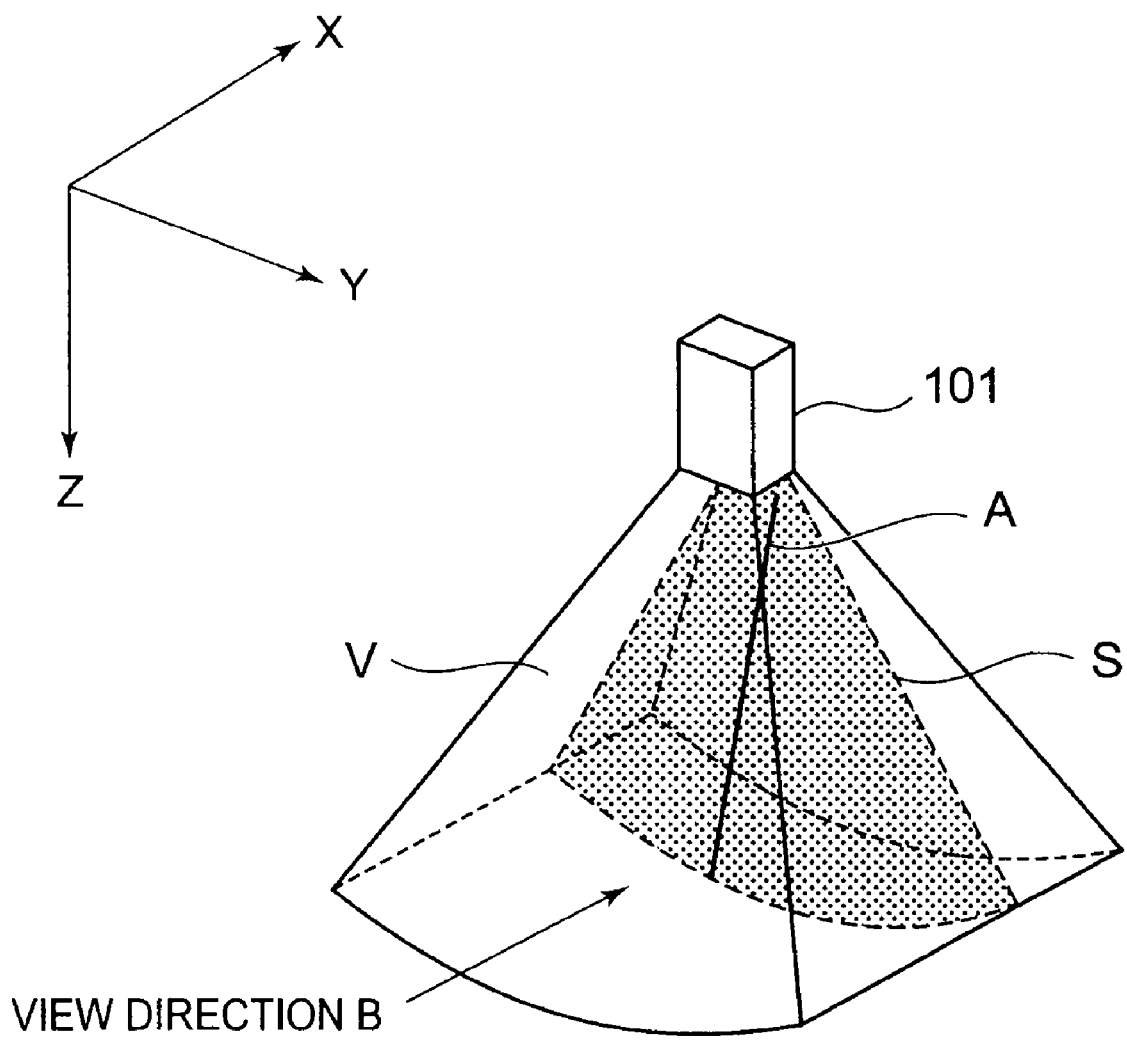
FIG. 2 is a view schematically showing a region scanned with ultrasound waves.

A region scanned by the ultrasound imaging apparatus 100 will be described with reference to FIG. 2. FIG. 2 is a view schematically showing a region scanned with ultrasound waves. For example, the ultrasound imaging apparatus 100 scans a three-dimensional region V within a subject with ultrasound waves by using an ultrasound probe 101 (volume scan). The ultrasound imaging apparatus 100 acquires volume data representing the three-dimensional region V in the volume scan. The volume data is stored into the image storing apparatus. Moreover, the volume data is outputted to the medical image processing apparatus 1 and stored into the image data storage 3.

This embodiment describes, as an example, a case of imaging the left ventricle of a heart and diagnosing an ischemic portion. With the heart of a subject as an imaging target, the ultrasound imaging apparatus 100 scans the heart with ultrasound waves to acquire volume data that represents a region including the left ventricle of the heart.

(Medical Image Processing Apparatus 1)

The medical image processing apparatus 1 is provided with a data transceiver 2, the image data storage 3, a cardiac cavity region specifying part 4, a rotation axis specifying part 5, a main controller 6, an input part 7, a display 8, and an image processor 10. The medical image processing apparatus 1 generates image data suitable for diagnosis of an ischemic portion based on the volume data acquired by the ultrasound imaging apparatus 100.

(Data Transceiver 2)

The data transceiver 2 receives the volume data via a network. To the network, an apparatus capable of supplying the volume data is connected. For example, the ultrasound imaging apparatus 100 and the not-shown image storing apparatus are connected to the network. The data transceiver 2 is connected to the network to receive volume data from the ultrasound imaging apparatus 100 or the image storing apparatus via the network. To the volume data, supplementary information including the patient name, examination ID and examination date is attached. The data transceiver 2 outputs the volume data to the image data storage 3.

(Image Data Storage 3)

The image data storage 3 stores the volume data outputted from the data transceiver 2. In this embodiment, volume data representing a region including the left ventricle of a heart is acquired by the ultrasound imaging apparatus 100, and the volume data is stored into the image data storage 3.

The image data storage 3 is composed of a storing device such as a hard disk drive and a semiconductor memory. Moreover, the image data storage 3 stores volume data outputted from the cardiac cavity region specifying part 4.

(Cardiac Cavity Region Specifying Part 4)

The cardiac cavity region specifying part 4 reads the volume data from the image data storage 3 and specifies the position of a cardiac cavity region in the left ventricle represented in the volume data. As a method of specifying the position of the cardiac cavity region, for example, it is possible to use any one of methods described in Japanese Unexamined Patent Publications Nos. 7-320068, 10-99328, 2000-217818, 2003-250804, 2005-161032 and 2000-210289.

For example, the cardiac cavity region specifying part 4 specifies the position of the cardiac cavity region by the boundary detection method using the luminance difference of volume data. For example, the cardiac cavity region specifying part 4 specifies the position of the cardiac cavity region in the left ventricle represented in volume data by binarizing volume data or differentiating pixel values. Moreover, the cardiac cavity region specifying part 4 may specify the position of the cardiac cavity region by using a contrast image. For example, imaging is conducted in a state that a contrast medium majorly including microbubbles is injected into a subject. Since the blood flow in the cardiac cavity is stained with higher luminance than the periphery, the cardiac cavity region specifying part 4 specifies the boundary of the cardiac cavity region by using the luminance difference and specifies the inside of the boundary as the cardiac cavity region.

The cardiac cavity region specifying part 4 defines the cardiac cavity region represented in the volume data as a region outside a display target. For example, the cardiac cavity region specifying part 4 executes a mask process on the cardiac cavity region represented in the volume data, thereby defining the cardiac cavity region as a region outside a display target. For example, the cardiac cavity region specifying part 4 converts the pixel values of pixels in the cardiac cavity region to given values in volume data. The cardiac cavity region specifying part 4 outputs the volume data in which the mask process has been executed on the cardiac cavity region, to the image data storage 3. The image data storage 3 stores the volume data having been subjected to the mask process.

(Rotation Axis Specifying Part 5)

The rotation axis specifying part 5 reads the volume data in which the cardiac cavity has been subjected to the mask process, from the image data storage 3. The rotation axis specifying part 5 then specifies the position of the long axis of the left ventricle represented in the volume data. The rotation axis specifying part 5 defines the specified long axis as a rotation axis with respect to an image generation plane. As a method of specifying the position of the long axis of the left ventricle, for example, it is possible to use any one of methods disclosed in Japanese Unexamined Patent Publications Nos. 7-320068, 10-99328, 2000-217818, 2003-250804, 2005-161032 and 2000-210289. For example, the rotation axis specifying part 5 approximates the stereoscopic left ventricle represented in the volume data by an ellipsoidal body. The rotation axis specifying part 5 specifies the long axis of the ellipsoidal body as the long axis of the left ventricle, and defines the specified long axis as the rotation axis. For example, as shown in FIG. 2, the rotation axis specifying part 5 specifies the position of a long axis A of the left ventricle in a three-dimensional region, and defines the long axis A as a rotation axis A. The rotation axis specifying part 5 outputs information (coordinate information) indicating the position of the rotation axis (long axis) A in the three-dimensional region to an image generation controller 11 of the image processor 10. Alternatively, the rotation axis specifying part 5 may specify the position of the short axis of the left ventricle and define the short axis as the rotation axis. For example, the rotation axis specifying part 5 specifies an axis orthogonal to the long axis as the short axis. Since there are a plurality of axes orthogonal to the long axis, the rotation axis specifying part 5 can select one of the axes as the short axis.

(Image Processor 10)

The image processor 10 includes the image generation controller 11, an image generation plane determining part 12, an image generator 13, a mask region changer 16 and a display controller 17. The image generator 13 includes a first image generator 14 and a second image generator 15. The display controller 17 includes an image synthesizer 18. The image processor 10 reads the volume data subjected to the mask process from the image data storage 3, and generates image data under image generation conditions outputted from the main controller 6. The image processor 10 then causes the display 8 to display an image based on the image data. The respective parts of the image processor 10 will be described below.

(Image Generation Controller 11)

The image generation controller 11 reads the volume data subjected to the mask process from the image data storage 3. Moreover, the image generation controller 11 receives the coordinate information of the rotation axis A outputted from the rotation axis specifying part 5. Moreover, the image generation controller 11 receives information indicating the image generation conditions outputted from the main controller 6. The image generation conditions include the type of an image to be generated and a view direction indicating a direction to generate an image. The image type includes a three-dimensional image generated by volume rendering, an MPR image, an MIP image, etc. An MPR image is an image in an arbitrary cross section generated by the MPR (Multi Planner Reconstruction) process. The image type and the view direction are previously set in the main controller 6.

Moreover, the operator can optionally change the image type and the view direction by using the input part 7.

The image generation controller 11 outputs the volume data subjected to the mask process, the information indicating the type of an image to be generated, and the information (coordinate information) of the view direction, to the first image generator 14 and the second image generator 15. Moreover, the image generator controller 11 outputs the coordinate information of the rotation axis A and the coordinate information of the view direction, to the image generation plane determining part 12.

(Image Generation Plane Determining Part 12)

The image generation plane determining part 12 receives the coordinate information of the rotation axis A and the coordinate information of the view direction that are outputted from the image generation controller 11. The image generation plane determining part 12 then specifies the position of a plane orthogonal to the view direction from among a plurality of two-dimensional planes passing the rotation axis A. The image generation plane determining part 12 determines the plane as a plane for generating an image (an image generation plane). For example, as shown in FIG. 2, the image generation plane determining part 12 defines a plane that passes through the rotation axis A and that is orthogonal to a view direction B, as an image generation plane S. The image generation plane determining part 12 then outputs the coordinate information of the image generation plane S that passes through the rotation axis A and that is orthogonal to the view direction, to the first image generator 14 and the second image generator 15.

(First Image Generator 14, Second Image Generator 15)

The first image generator 14 and the second image generator 15 receive the volume data subjected to the mask process, the information indicating the type of an image to be generated and the coordinate information indicating the view direction, from the image generation controller 11. Moreover, the first image generator 14 and the second image generator 15 receive the coordinate information of the image generation plane S, from the image generation plane determining part 12. The first image generator 14 and the second image generator 15 then generate image data for display based on the volume data, respectively.

In this embodiment, the image generation controller 11 provides the first image generator 14 with an instruction to generate a three-dimensional image by volume rendering. Moreover, the image generation controller 11 provides the second image generator 15 with an instruction to generate an MPR image. In other words, the image generation controller 11 outputs information that indicates a three-dimensional image as the type of a generated image to the first image generator 14, and outputs information that indicates an MPR image as the type of a generated image to the second image generator 15.

The first image generator 14 executes volume rendering along the view direction B on the volume data subjected to the mask process, thereby generating three-dimensional image data that stereoscopically indicates the tissue. In this embodiment, the first image generator 14 generates three-dimensional image data based on data, excluding data included in a region in front of the image generation plane S taken from the view direction B and data included in a region subjected to the mask process. Consequently, in a region subjected to the mask process, three-dimensional image data will not be generated in a region up to the boundary of the region subjected to the mask process in a region in rear of the image generation plane S taken from the view direction B. In other words, the region subjected to the mask process will not be represented in the three-dimensional image data.

Since the mask process has been executed on the cardiac cavity region, the first image generator 14 generates three-dimensional image data based on data, excluding data included in the region in front of the image generation plane S taken from the view direction B and data included in the cardiac cavity region subjected to the mask process. Consequently, in a region in which the cardiac cavity region exists, three-dimensional image data will not be generated in the region up to the boundary of the region subjected to the mask process in the region in rear of the image generation plane S taken from the view direction. In other words, the cardiac cavity region subjected to the mask process will not be represented in the three-dimensional image data. As a result, in the three-dimensional image data, a surface of a myocardial region, which is a surface of the myocardial region in rear of the image generation plane S taken from the view direction B, is represented at the position of the region in which the cardiac cavity region exists. The first image generator 14 may generate shadowed three-dimensional image data by executing a shadowing process.

On the other hand, the second image generator 15 executes an MPR process on the volume data subjected to the mask process, thereby generating MPR image data in the image generation plane S. In this embodiment, the second image generator 15 generates MPR image data in the image generation plane S based on data excluding data included in the region subjected to the mask process. Since the mask process has been executed on the cardiac cavity region, the second image generator 15 generates MPR image data in the image generation plane S based on data excluding data included in the cardiac cavity region. Consequently, in the MPR image data, the cardiac cavity region is not represented, and the myocardial region in the image generation plane S is represented.

The first image generator 14 outputs the three-dimensional image data generated by volume rendering to the display controller 17. The second image generator 15 outputs the MPR image data generated by the MPR process to the display controller 17.

Figure 3A:
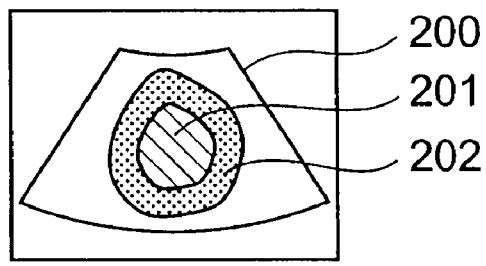
FIG. 3A is a view schematically showing an image generated by the medical image processing apparatus according to the embodiment of the present invention.
Figure 3B:
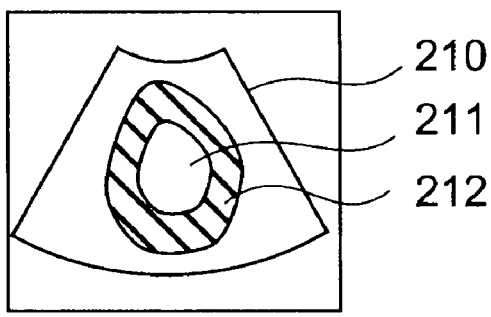
FIG. 3B is a view schematically showing an image generated by the medical image processing apparatus according to the embodiment of the present invention.
Figure 3C:
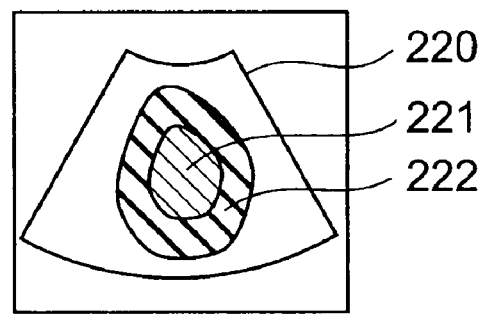
FIG. 3C is a view schematically showing an image generated by the medical image processing apparatus according to the embodiment of the present invention.

A three-dimensional image generated by the first image generator 14 and an MPR image generated by the second image generator 15 are shown in FIGS. 3A, 3B and 3C. FIGS. 3A, 3B and 3C are views schematically showing an image generated by the medical image processing apparatus according to the embodiment of the present invention.

A three-dimensional image 200 shown in FIG. 3A is a three-dimensional image generated by the first image generator 14. An MPR image 210 shown in FIG. 3B is an MPR image generated by the second image generator 15.

The mask process has been executed on the cardiac cavity region represented in the volume data. The three-dimensional image 200 is a three-dimensional image generated based on data, excluding data included in the cardiac cavity region and data included in the region in front of the image generation plane S taken from the view direction B. Therefore, the cardiac cavity region subjected to the mask process is not shown in the three-dimensional image 200. Since the cardiac cavity region has been subjected to the mask process, three-dimensional image data will not be generated in a region up to the endocardium of the myocardial region in the region in rear of the image generation plane S taken from the view direction B in the region in which the cardiac cavity region exists. Thus, in the region in which the cardiac cavity region exists, the three-dimensional image data in the region from the image generation plane S to the endocardium of the myocardium is not generated, and therefore, the region from the image generation plane S to the endocardium of the myocardium is not displayed. Accordingly, in the three-dimensional image 200 shown in FIG. 3A, the cardiac cavity region is not shown at the position of the region in which the cardiac cavity region exists, and a surface of the myocardium, which is an endocardium 201 of the myocardium in rear of the image generation plane S taken from the view direction B, is shown. Moreover, a myocardial region 202 around the cardiac cavity region is shown in the three-dimensional image 200.

Further, the MPR image 210 shown in FIG. 3B is an MPR image generated based on data excluding data included in the cardiac cavity region.

Therefore, a cardiac cavity region 211 subjected to the mask process is not shown in the MPR image 210. In the MPR image 210, a myocardial region 212 in the image generation plane S is shown.

(Display Controller 17)

The display controller 17 receives the three-dimensional image data outputted from the first image generator 14 and the MPR image data outputted from the second image generator 15, and causes the display 8 to display a three-dimensional image and an MPR image. The display controller 17 includes the image synthesizer 18.

(Image Synthesizer 18)

The image synthesizer 18 synthesizes the three-dimensional image data generated by the first image generator 14 and the MPR image data generated by the second image generator 15, thereby generating synthesized image data. In this embodiment, the image synthesizer 18 synthesizes the three-dimensional image data representing the inner face of the myocardium with the region in which the cardiac cavity region exists in the MPR image data representing the myocardial region. Otherwise, the image synthesizer 18 may synthesize the MPR image data representing the myocardial region with a region in which the myocardial region exists except the region in which the cardiac cavity region exists, in the three-dimensional image data representing the inner face of the myocardium. In other words, the image synthesizer 18 uses the MPR image data for the myocardial region and uses the three-dimensional image data representing the inner face of the myocardium for the region in which the cardiac cavity region exists, thereby synthesizing the MPR image data and the three-dimensional image data. Consequently, the image synthesizer 18 generates synthesized image data in which the myocardial region is represented by the MPR image in the image generation plane S and the endocardium of the myocardium in rear of the image generation plane S taken from the view direction B is represented by the three-dimensional image.

The display controller 17 causes the display 8 to display a synthesized image based on the synthesized image data. FIG. 3C shows an example of the synthesized image. The MPR image data in the image generation plane S is used for the myocardial region, and the three-dimensional image data representing the endocardium of the myocardium is used for the region in which the cardiac cavity region exists. Therefore, in a synthesized image 220, a myocardial region 222 is shown with an MPR image, and an endocardium 221 of the myocardium is shown with a three-dimensional image. Since the cardiac cavity region is subjected to the mask process, the cardiac cavity region will not be shown at the position of the region in which the cardiac cavity region exists. Since the three-dimensional image data in the region from the image generation plane S to the endocardium of the myocardium is not generated in the region in which the cardiac cavity region exists, the region from the image generation plane S to the endocardium of the myocardium will not be displayed. Therefore, in the synthesized image 220 shown in FIG. 3C, at the position of the region in which the cardiac cavity region exists, a surface of the myocardium, which is the endocardium 221 of the myocardium in rear of the image generation plane S taken from the view direction B, is shown as a three-dimensional image. A region outside the myocardial region may be shown with an MPR image or a three-dimensional image.

(Input Part 7, Display 8)

The input part 7 is composed of a pointing device like a mouse and a trackball, a switch, various types of buttons, a keyboard, etc. The operator can input the image generation conditions such as the type of an image to be generated and the view direction by using the input part 7. Moreover, the display 8 is composed of a monitor such as a CRT and a liquid crystal display.

On the display 8, a synthesized image is displayed.

(Main Controller 6)

The main controller 6 controls the operations of the data transceiver 2, the cardiac cavity region specifying part 4, the rotation axis specifying part 5 and the image processor 10. In the main controller 6, the information indicating the type of an image to be generated and the information indicating the view direction are previously set. The main controller 6 outputs the information showing the image generation conditions including the type of an image and the view direction to the image generation controller 11 of the image processor 10, and provides the image generation controller 11 with an instruction to generate an image. The size of the mask region may also be included in the image generation conditions. In this case, the main controller 6 outputs information indicating the image generation conditions including the size of the mask region to the image generation controller 11. The image generation controller 11 outputs the information indicating the size of the mask region and the volume data having been subjected to the mask process to the mask region changer 16.

As described above, the medical image processing apparatus 1 according to the embodiment displays the endocardium of the myocardial region with a three-dimensional image, and displays the cross section of the myocardial region with an MPR image, whereby it is possible to stereoscopically display and observe the endocardium of the myocardial region and also observe the cross section of the myocardium with the MPR image.

By displaying the myocardial region with an MPR image, it is possible to display distribution of lesion sites such as myocardial infarction in the myocardial region so that the operator can easily understand. In other words, the myocardial region is easy to observe when displayed with an MPR image.

Therefore, when the myocardial region is displayed with an MPR image, the operator can easily see distribution of lesion sites such as myocardial infarction in the myocardial region. For example, it becomes easier to grasp how the myocardial infarction distributes from the inside to outside of the myocardial region. Thus, the medical image processing apparatus 1 according to the embodiment can provide an image by which it is easy to assess a lesion site such as myocardial infarction.

(Change of Position of Image Generation Plane S)

Next, change of the position of the image generation plane S will be described. The operator can input an angle for changing the image generation plane by using the input part 7 while observing the synthesized image 220 displayed on the display 8. To be specific, the operator can input the angle by moving the mouse or rotating the track ball. Information representing the movement amount of the mouse or information representing the rotation amount of the track ball is outputted from the input part 7 to the main controller 6. The movement amount of the mouse or the rotation amount of the track ball corresponds to the change amount of the angle. Based on the view direction set in advance and the change amount of the angle inputted from the input part 7, the main controller 6 obtains a new view direction. The main controller 6 outputs coordinate information indicating the newly obtained view direction to the image generation controller 11 of the image processor 10.

The image generation controller 11 outputs the coordinate information indicating the new view direction to the image generation plane determining part 12. Based on the coordinate information of the rotation axis A and the coordinate information indicating the new view direction, the image generation plane determining part 12 determines, as a new image generation plane S, a plane orthogonal to the new view direction from among a plurality of two-dimensional planes passing through the rotation axis A. The image generation plane determining part 12 then outputs the coordinate information of the new image generation plane S to the first image generator 14 and the second image generator 15. Moreover the image generation controller 11 outputs the coordinate information showing the new view direction to the first image generator 14 and the second image generator 15.

As described above, the first image generator 14 executes volume rendering along a new view direction B on the volume data subjected to the mask process, thereby generating three-dimensional image data that stereoscopically represents the tissue. The first image generator 14 generates three-dimensional image data based on data, excluding data included in a region in front of a new image generation plane S taken from the new view direction B and data included in the cardiac cavity region subjected to the mask process. Consequently, in the newly generated three-dimensional image data, a surface of the myocardial region, which is a surface in rear of the new image generation plane S taken from the new view direction B, is represented.

Further, as described above, the second image generator 15 executes the MPR process on the volume data subjected to the mask process, thereby generating MPR image data in the new image generation plane S. The second image generator 15 generates the MPR image data in the new image generation plane S based on data excluding data included in the cardiac cavity region subjected to the mask process. Consequently, in the newly generated MPR image data, the cardiac cavity region is not represented, and a myocardial region in the new image generation plane S is represented.

Then, the image synthesizer 18 synthesizes the newly generated three-dimensional image data and the newly generated MPR image data, thereby generating new synthesized image data. Consequently, the image synthesizer 18 generates synthesized image data in which the myocardial region is represented by the MPR image in the new image generation plane S and the endocardium of the myocardium in rear of the new image generation plane S taken from the new view direction B is represented by the three-dimensional image. Then, the display controller 17 causes the display 8 to display a synthesized image based on the newly generated synthesized image data.

By repeating the operation of changing the angle by the operator and the process by the image processor 10, the operator can continuously observe synthesized images in different image generation planes S.

Figure 4:
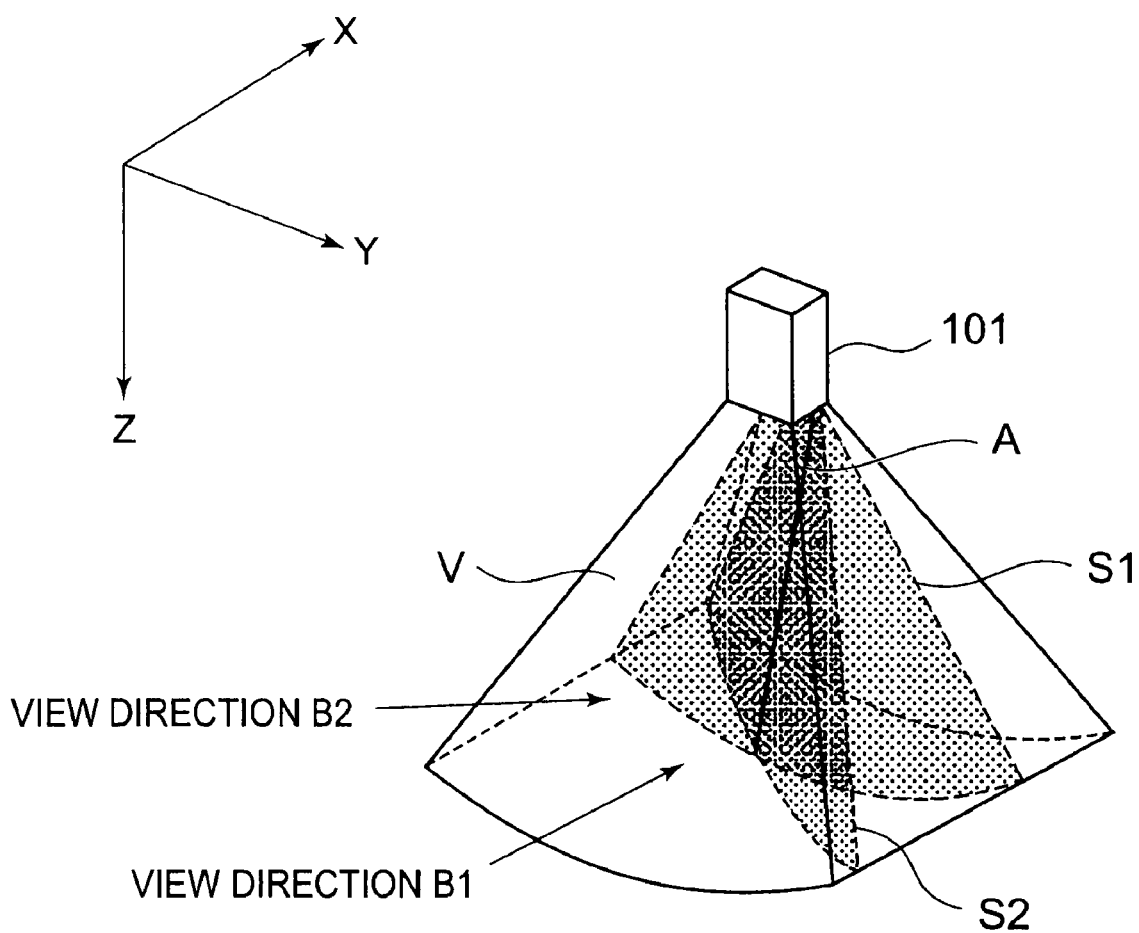
FIG. 4 is a view schematically showing a region scanned with ultrasound waves.
Figure 5A:
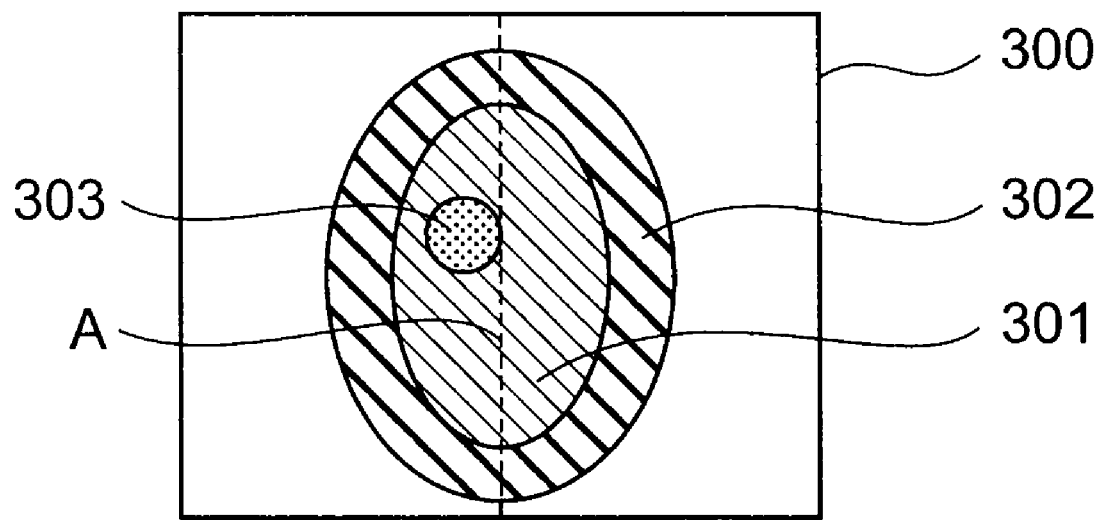
FIG. 5A is a view schematically showing an image generated by the medical image processing apparatus according to the embodiment of the present invention.
Figure 5B:
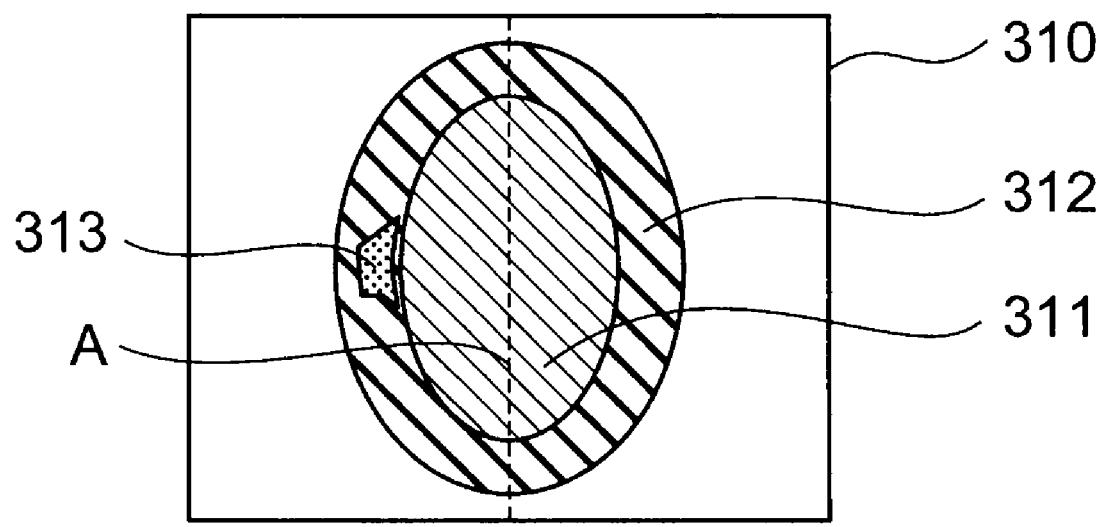
FIG. 5B is a view schematically showing an image generated by the medical image processing apparatus according to the embodiment of the present invention.

Now, an example of an image obtained in a case myocardial infarction exists and the position of the image generation plane is changed will be described with reference to FIGS. 4, 5A and 5B. FIG. 4 is a view schematically showing a region scanned with ultrasound waves. FIGS. 5A and 5B are views schematically showing an image generated by the medical image processing apparatus according to the embodiment of the present invention.

A view direction B1 shown in FIG. 4 is an initially set view direction, and an image generation plane S1 is a plane orthogonal to the view direction B1. The first image generator 14 and the second image generator 15 generate image data by using the view direction B1 and the image generation plane S1, respectively. As described above, the first image generator executes volume rendering along the view direction B1 on the volume data subjected to the mask process, thereby generating three-dimensional image data that stereoscopically represents the tissue. The first image generator 14 generates the three-dimensional image data based on data, excluding data included in a region in front of the image generation plane S1 taken from the view direction B1 and data included in the cardiac cavity region subjected to the mask process. Moreover, the second image generator 15 executes the MPR process on the volume data having been subjected to the mask process, thereby generating MPR image data in the image generation plane S1. The second image generator 15 generates the MPR image data in the image generation plane S1 based on data excluding data included in the cardiac cavity region subjected to the mask process. Then, the image synthesizer 18 synthesizes the three-dimensional image data and the MPR image data, thereby generating synthesized image data. The display controller 17 causes the display 8 to display a synthesized image based on the synthesized image data.

A synthesized image 300 shown in FIG. 5A is an image generated by using the view direction B1 and the image generation plane S1. The MPR image data in the image generation plane S1 is used for the myocardial region, and the three-dimensional image data representing the endocardium of the myocardium is used for the region in which the cardiac cavity region exists.

Therefore, in the synthesized image 300, a myocardial region 302 is shown with the MPR image, and an endocardium 301 of the myocardium is shown with the three-dimensional image. Since the cardiac cavity region has been subjected to the mask process, a surface of the myocardium, which is the endocardium 301 of the myocardium in rear of the image generation plane S1 taken from the view direction B1, is shown as a three-dimensional image in the synthesized image 300, in the position of the region in which the cardiac cavity region exists. In the synthesized image 300, myocardial infarction 303 is shown on the opposite side across the cardiac cavity region taken from the view direction B1. This myocardial infarction 303 is shown as a three-dimensional image.

Since use of an MPR image makes it easier to assess myocardial infarction, the operator changes the view direction so that the myocardial infarction is shown in the MPR image. As described above, the operator inputs an angle by using the input part 7 while observing the synthesized image displayed on the display 8. A view direction B2 shown in FIG. 4 is a view direction designated by the operator, and an image generation plane S2 is a plane orthogonal to the view direction B2. As described above, the first image generator 14 executes volume rendering along the view direction B2 on the volume data subjected to the mask process, thereby generating three-dimensional image data that stereoscopically represents the tissue. The first image generator 14 generates the three-dimensional image data based on data, excluding data included in a region in front of the image generation plane B2 taken from the view direction B2 and data included in the cardiac cavity region subjected to the mask process. Moreover, the second image generator 15 executes the MPR process on the volume data subjected to the mask process, thereby generating MPR image data in the image generation plane S2.

The second image generator 15 generates the MPR image data in the image generation plane S2 based on data excluding data included in the cardiac cavity region subjected to the mask process. Then, the image synthesizer 18 synthesizes the three-dimensional image data and the MPR image data, thereby generating synthesized image data. The display controller 17 causes the display 8 to display a synthesized image based on the synthesized image data.

A synthesized image 310 shown in FIG. 5B is an image generated by using the view direction B2 and the image generation plane S2. The MPR image data in the image generation plane S2 is used for the myocardial region, and the three-dimensional image data representing the endocardium of the myocardium is used for the region in which the cardiac cavity region exists.

Therefore, in the synthesized image 310, a myocardial region 312 is shown with the MPR image, and an endocardium 311 of the myocardium is shown with the three-dimensional image. Since the cardiac cavity region has been subjected to the mask process, a surface of the myocardium, which is the endocardium 311 of the myocardium in rear of the image generation plane S2 taken from the view direction B2, is shown as the three-dimensional image in the position of the region in which the cardiac cavity region exists in the synthesized image 310. In this synthesized image 310, myocardial infarction 313 is shown in the myocardial region 312 shown with the MPR image. In a case that the image generation plane S2 is set at a position passing through the myocardial infarction, the myocardial infarction 313 is shown in the myocardial region 312 shown with the MPR image. Since the myocardial region 312 is shown with the MPR image, it is possible to assess the myocardial infarction by using such MPR image that facilitates assessment.

Thus, it is possible to display the myocardial infarction with the MPR image, depending on a position in which the image generation plane is set.

Consequently, the observer can observe the distribution state of the myocardial infarction in the image generation plane. For example, by observing the MPR image, the observer can easily grasp how the myocardial infarction in the myocardial region distributes from the inside to outside of the myocardial region.

(Mask Region Changer 16)

The mask region changer 16 receives information indicating the size of the mask region and the volume data subjected to the mask process, from the image generation controller 11. The mask region changer 16 changes the size of the mask region in the volume data in accordance with the information indicating the size of the mask region. The mask region changer 16 changes the size of the mask in the volume data by executing the dilation process or erosion process according to known techniques. Consequently, in the volume data, the size of a region outside a display target is changed. For example, the mask region changer 16 changes the pixel values of pixels within a region included in the mask with the size changed in the volume data, to given values. The mask region changer 16 outputs the volume data subjected to a new mask process, to the first image generator 14 and the second image generator 15. However, in a case that there is no change of the size of the mask region, the mask region changer 16 does not execute the process. The first image generator 14 generates three-dimensional image data based on the volume data subjected to the new mask process. Moreover, the second image generator 15 generates MPR image data based on the volume data subjected to the new mask process.

Now, the change of the size of the mask region will be described with reference to FIG. 6. FIG. 6 is a schematic view for describing the size of the mask region. In the case of dilating the mask region, the mask region changer 16 increases the size of a mask 401 in the initial state based on the information indicating the size of the mask region and changes the mask 401 to a mask 402. The mask region changer 16 executes the mask process on the volume data with the new mask 402, and outputs the volume data subjected to the mask process to the first image generator 14 and the second image generator 15. In the case of eroding the mask region, the mask region changer 16 decreases the size of the mask based on the information indicating the size of the mask region and changes the mask to a mask 403. The mask region changer 16 executes the mask process on the volume data with the new mask 403, and outputs the volume data subjected to the mask process to the first image generator 14 and the second image generator 15. The first image generator 14 generates three-dimensional image data based on the volume data subjected to the mask process with the mask 402 or the mask 403.

Moreover, the second image generator 15 generates MPR image data based on the volume data subjected to the mask process with the mask 402 or the mask 403.

For example, the operator gives an instruction to dilate or erode the mask region by using the input part 7. Moreover, the operator inputs the information indicating the level of dilation or erosion by using the input part 7. For example, the operator gives dilatability or erodibility. To be specific, the operator gives a numerical value such as 120% and 80% by using the input part 7. In a case that an instruction to execute the dilation process and the dilatability are given with the input part 7, information indicating the dilation process and information indicating the dilatability are outputted from the input part 7 to the main controller 6. The main controller 6 includes the dilatability of the mask region into the image generation conditions, and outputs information indicating the image generation conditions to the image generation controller 11 of the image processor 10. The image generation controller 11 outputs, to the mask region changer 16, the volume data having been subjected to the mask process and the information indicating the dilatability. The mask region changer 16 increases the mask at the dilatability and executes the mask process on the volume data with the dilated mask.

Then, the mask region changer 16 outputs the volume data newly subjected to the mask process to the first image generator 14 and the second image generator 15.

The first image generator 14 generates three-dimensional image data based on the volume data subjected to the mask process with the dilated mask.

Moreover, the second image generator 15 generates MPR image data based on the volume data subjected to the mask process with the dilated mask.

The image synthesizer 18 generates synthesized image data by synthesizing the three-dimensional image data and the MPR image data.

Figure 7A:
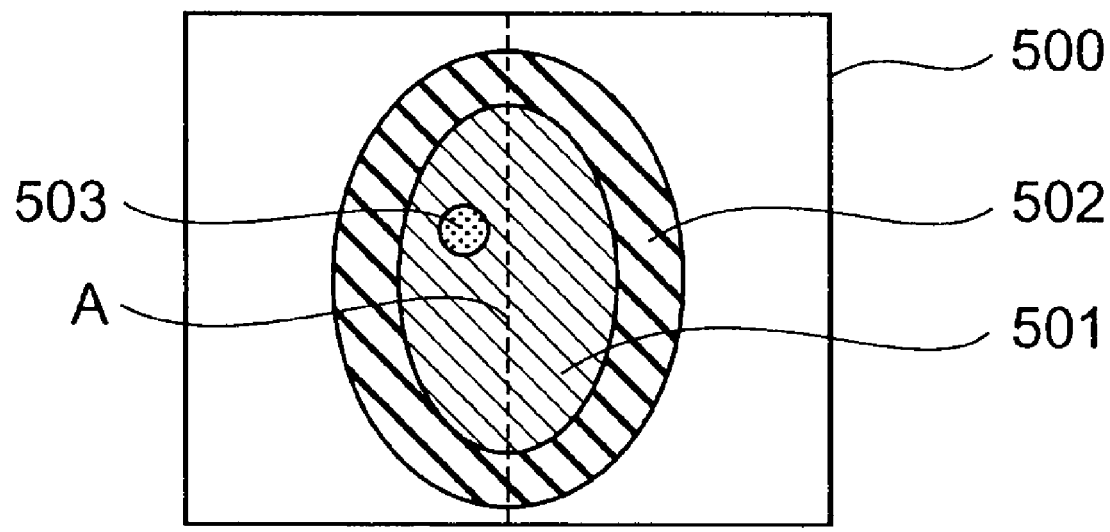
FIG. 7A is a view schematically showing a synthesized image generated before the mask region is changed.
Figure 7B:
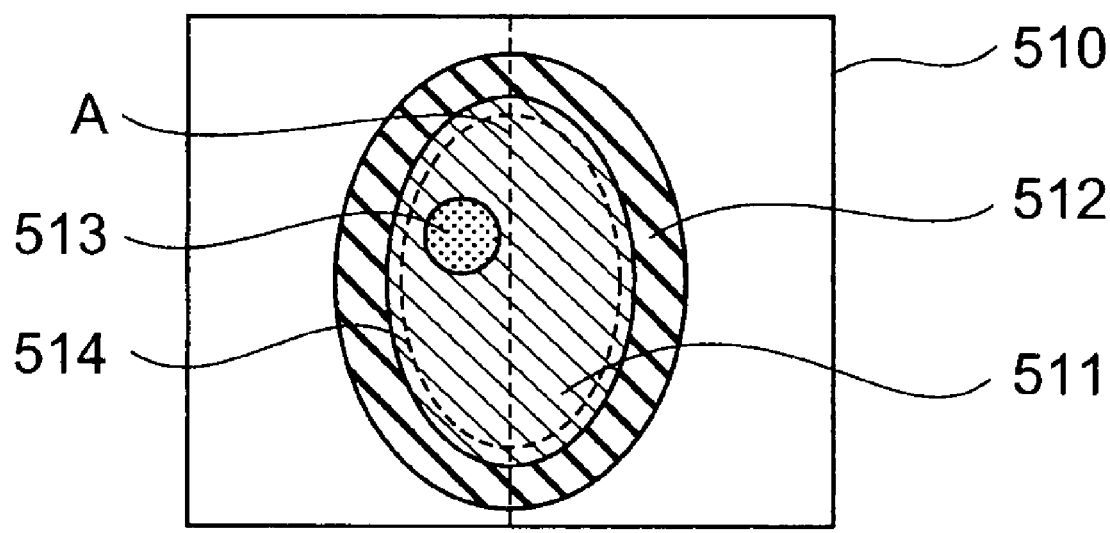
FIG. 7B is a view schematically showing a synthesized image generated after the mask region is changed.

The synthesized image data generated before the dilation of the mask region and the synthesized image data generated after the dilation are shown in FIGS. 7A and 7B. FIG. 7A is a view schematically showing a synthesized image generated before the mask region is changed. FIG. 7B is a view schematically showing a synthesized image generated after the mask region is changed. A synthesized image 500 shown in FIG. 7A is an image generated before the mask region is dilated. MPR image data in the image generation plane S is used for a myocardial region 502, and three-dimensional image data representing the endocardium of the myocardium is used for the region in which the cardiac cavity region exists. Therefore, in the synthesized image 500, a myocardial region 502 is shown with an MPR image, and an endocardium 501 of the myocardium is shown with a three-dimensional image.

In this synthesized image 500, myocardial infarction 503 is shown on the opposite side across the cardiac cavity region taken from the view direction B1. This myocardial infarction 503 is shown with a three-dimensional image.

On the other hand, a synthesized image 510 shown in FIG. 7B is an image generated after the mask region is dilated. Since the mask region has been dilated, a region shown with an MPR image is smaller than in the synthesized image 500. In the synthesized image 510, a myocardial region 512 is shown with an MPR image, and a region inside the myocardial region 512 is shown with a three-dimensional image. Since the mask region has been dilated, the mask process is also executed on the inside of the myocardial region. Therefore, an inside 511 of the myocardial region is shown with a three-dimensional image. Consequently, myocardial infarction distributed inside the myocardial region is shown with a three-dimensional image, and therefore, assessment of the myocardial infarction is facilitated.

Further, the first image generator 14 may obtain the position of the boundary of a region in which the mask region is cut by the image generation plane S, based on volume data in which the size of the mask region is not changed. Then, the first image generator 14 outputs coordinate information indicating the boundary to the display controller 17. The display controller 17 causes the display 8 to display a boundary line indicating the boundary so as to be superimposed on a synthesized image. For example, as shown in FIG. 7B, the display controller 17 causes the display 8 to display the synthesized image 510 and display a boundary line 514 so as to be superimposed on the synthesized image 510. The boundary line 514 is a line indicating the range of the mask region before the dilation.

As described above, it is possible to, by changing the size of the mask region, generate and display a three-dimensional image that stereoscopically shows the tissue inside the myocardial region not only the surface of the myocardial region. That is to say, it is possible to, by increasing the size of the mask region and including the inside of the myocardial region into the mask region, generate and display a three-dimensional image showing the tissue inside the myocardial region. Thus, by stereoscopically displaying myocardial infarction distributed inside the myocardial region, it is possible to provide information used for assessment of the myocardial infarction.

(Modification 1)

In a Modification 1, a Plurality of Image Generation Planes are obtained, and synthesized image data in the respective image generation planes are generated. As an example, generation of two synthesized image data will be described. As described above, the image generation plane determining part 12 receives the coordinate information of the rotation axis A and the coordinate information of the view direction outputted from the image generation controller 11, and determines, as a first image generation plane, a plane orthogonal to the view direction from among a plurality of planes passing through the rotation axis A. Furthermore, the image generation plane determining part 12 determines a plane orthogonal to the first image generation plane and passing through the rotation axis A, as a second image generation plane. The image generation plane determining part 12 outputs the coordinate information of the first image generation plane and the coordinate information of the second image generation plane, to the first image generator 14 and the second image generator 15.

The first image generator 14 executes volume rendering on the volume data subjected to the mask process, by using the first image generation plane and the view direction orthogonal to the first image generation plane, thereby generating first three-dimensional image data. That is to say, the first image generator 14 generates the first three-dimensional image data based on data, excluding data included in a region in front of the first image generation plane taken from the view direction and data included in the region subjected to the mask process. On the other hand, the second image generator 15 executes the MPR process on the volume data subjected to the mask process, thereby generating first MPR image data in the first image generation plane.

The image synthesizer 18 synthesizes the first three-dimensional image data and the first MPR image data, thereby generating first synthesized image data.

Similarly, the first image generator 14 executes volume rendering on the volume data subjected to the mask process, by using the second image generation plane and the view direction orthogonal to the second image generation plane, thereby generating second three-dimensional image data.

That is to say, the first image generator 14 generates the second three-dimensional image data based on data, excluding data included in a region in front of the second image generation plane taken from the view direction and data included in the region subjected to the mask process. On the other hand, the second image generator 15 executes the MPR process on the volume data subjected to the mask process, thereby generating second MPR image data in the second image generation plane. The image synthesizer 18 synthesizes the second three-dimensional image data and the second MPR image data, thereby generating second synthesized image data.

The display controller 17 causes the display 8 to simultaneously display a first synthesized image based on the first synthesized image data and a second synthesized image based on the second synthesized image data.

The first synthesized image and the second synthesized image displayed on the display 8 are shown in FIG. 8. FIG. 8 is a view schematically showing an image generated by the medical image processing apparatus according to the embodiment of the present invention.

The display controller 17 causes the display 8 to simultaneously display a first synthesized image 600 and a second image synthesized image 610 side by side. Since the first image generation plane and the second image generation plane are orthogonal to each other, the first synthesized image 600 and the second synthesized image 610 are images in the mutually orthogonal planes. In the first synthesized image 600, a myocardial region 602 is shown with an MPR image, and an endocardium 601 of the myocardium is shown with a three-dimensional image. Since the cardiac cavity region has been subjected to the mask process, a surface of the myocardium, which is the endocardium 601 of the myocardium in rear of the first image generation plane taken from the view direction, is shown as a three-dimensional image, at the position of the region in which the cardiac cavity region exists in the first synthesized image 600. In the first synthesized image 600, myocardial infarction 603 is shown on the opposite side across the cardiac cavity region taken from the view direction. The myocardial infarction 603 is shown with a three-dimensional image.

Also in the second synthesized image 610, a myocardial region 612 is shown with an MPR image and an endocardium 611 of the myocardium is shown with a three-dimensional image. Since the cardiac cavity region has been subjected to the mask process, a surface of the myocardium, which is the endocardium 611 of the myocardium in rear of the second image generation plane taken from the view direction, is shown as a three-dimensional image at the position of the region in which the cardiac cavity region exists in the second synthesized image 610.

By setting the direction of the first image generation plane so that the myocardial infarction 603 is shown on the rotation axis A in the first synthesized image 600, a myocardial infarction site 613 is shown in the MPR image in the second synthesized image 610. That is to say, the second image generation plane is defined as a plane passing through the rotation axis A and orthogonal to the first image generation plane. Therefore, by setting the direction of the first image generation plane so that the myocardial infarction 603 shown in the first synthesized image 600 is shown on the rotation axis A, it is possible to set the second image generation plan at a position intersecting the myocardial infarction. Thus, it is possible to display the myocardial infarction 613 in the MPR image showing the myocardial region in the second synthesized image 610. In order to change the direction of the first image generation plane, as described above, the operator can input an angle to change the direction of the first image generation plane by using the input part 7. For example, the operator may input an angle of the first image generation plane by using the input part 7 so that the myocardial infarction 603 is shown on the rotation axis A in the first synthesized image 600, while observing the first synthesized image 600 and the second synthesized image 610 displayed on the display 8.

As described above, according to the modification 1, it is possible to display the myocardial infarction with a three-dimensional image in the first synthesized image 600, and display the myocardial infarction with an MPR image in the second synthesized image 610. Since it is possible to observe distribution of the myocardial infarction with the three-dimensional image and the MPR image simultaneously, assessment of the myocardial infarction is further facilitated.

Further, it is possible to fix the position of either the first image generation plane or the second image generation plane, and change only the angle of the other. For example, it is possible to fix the position of the first image generation plane, and change only the angle of the second image generation plane. Moreover, although the first image generation plane and the second image generation plane are orthogonal to each other in the modification 1, they may intersect at an arbitrary angle. For example, the operator may input the direction (angle) of the first image generation plane and the direction (angle) of the second image generation plane by using the input part 7, and make the first image generation plane and the second image generation plane intersect each other at an arbitrary angle.

(Modification 2)

Figure 9:
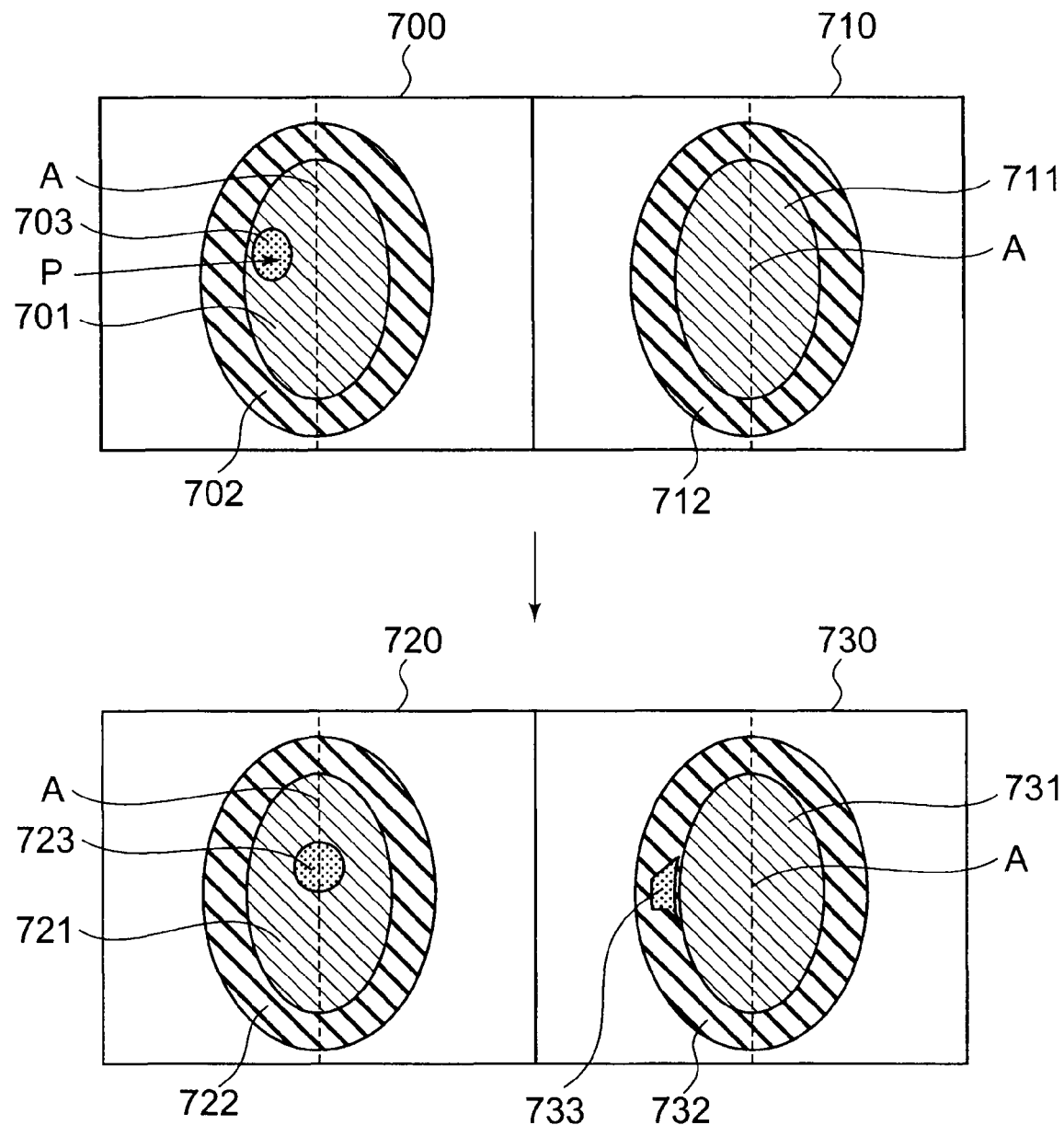
FIG. 9 is a view schematically showing an image generated by the medical image processing apparatus according to the embodiment of the present invention.

Next, a modification 2 will be described with reference to FIG. 9. FIG. 9 is a view schematically showing an image generated by the medical image processing apparatus according to the embodiment of the present invention.

As in the modification 1 described above, the display controller 17 causes the display 8 to display two synthesized images in mutually orthogonal image generation planes. For example, as shown in FIG. 9, the display controller 17 causes the display 8 to simultaneously display a first synthesized image 700 generated by using the first image generation plane and a second synthesized image 710 generated by using the second image generation plane side by side. As in the modification 1, the first image generation plane and the second image generation plane are orthogonal to each other. Therefore, the first synthesized image 700 and the second synthesized image 710 are images in the mutually orthogonal planes.

In the first synthesized image 700, a myocardial region 702 is shown with an MPR image, and an endocardium 701 of the myocardium is shown with a three-dimensional image. Since the cardiac cavity region has been subjected to the mask process, a surface of the myocardium, which is the endocardium 701 of the myocardium in rear of the first image generation plane taken from the view direction, is shown as a three-dimensional image in the position of the region in which the cardiac cavity region exists in the first synthesized image 700. In the first synthesized image 700, myocardial infarction 703 is shown on the opposite side across the cardiac cavity region taken from the view direction. This myocardial infarction 703 is shown with a three-dimensional image. Also in the second synthesized image 710, a myocardial region 712 is shown with an MPR image, and an endocardium 711 of the myocardium is shown with a three-dimensional image. Since the cardiac cavity region has been subjected to the mask process, a surface of the myocardium, which is the endocardium 711 of the myocardium in rear of the second image generation plane taken from the view direction, is shown as a three-dimensional image in the position of the region in which the cardiac cavity region exists in the second synthesized image 710.

Although the myocardial infarction 703 is shown within the three-dimensional image in the first synthesized image 700, the myocardial infarction is not shown in the second synthesized image 710. The second image generation plane is a plane passing through the rotation axis A and orthogonal to the first image generation plane. Although the myocardial infarction 703 is shown in the first synthesized image 700, it is shown in a position off the rotation axis A. Therefore, the myocardial infarction does not exist in the second image generation plane passing through the rotation axis A and orthogonal to the first image generation plane. Consequently, the myocardial infarction is not shown in the second synthesized image.

If the direction of the first image generation plane is set so that the myocardial infarction 703 is shown on the rotation axis A in the first synthesized image 700, the myocardial infarction is also shown in the second synthesized image as in the modification 1. In the modification 2, a process for facilitating the setting of the image generation plane is conducted. The process according to the modification 2 will be described below.

The operator gives an instruction to change the image generation plane by using the input part 7, and further designates the myocardial infarction 703 shown on the display 8. For example, the operator designates an optional point P within the myocardial infarction 703. When the optional point P is thus designated, coordinate information of the point P is outputted from the input part 7 to the main controller 6. The main controller 6 outputs the coordinate information of the point P to the image generation controller 11, and the image generation controller 11 outputs the coordinate information of the point P to the image generation plane determining part 12.

Upon reception of the coordinate information of the point P, the image generation plane determining part 12 obtains a line that passes through the point P and is orthogonal to the first image generation plane. Next, the image generation plane determining part 12 obtains the intersection of the line with the surface of the mask region. The image generation plane determining part 12 obtains the intersection of the line with the surface of the mask region in rear of the first image generation plane taken from the view direction set with respect to the first image generation plane. Next, the image generation plane determining part 12 obtains a plane that passes through the intersection and the rotation axis A, and determines the plane as a new second image generation plane. The position of the second image generation plane intersecting with the myocardial infarction is thus obtained.

Furthermore, the image generation plane determining part 12 determines a plane that is orthogonal to the new second image generation plane and passes through the rotation axis A, as a new first image generation plane. The image generation plane determining part 12 outputs coordinate information of the new first image generation plane and coordinate information of the new second image generation plane, to the first image generator 14 and the second image generator 15.

The first image generator 14 executes volume rendering on the volume data subjected to the mask process, by using the new first image generation plane and the view direction orthogonal to the first image generation plane, thereby generating new first three-dimensional image data. On the other hand, the second image generator 15 executes the MPR process on the volume data subjected to the mask process, thereby generating new first MPR image data in the new first image generation plane. The image synthesizer 18 synthesizes the new first three-dimensional image data and the new first MPR image data, thereby generating new first synthesized image data.

Similarly, the first image generator 14 executes volume rendering on the volume data subjected to the mask process, by using the new second image generation plane and the view direction orthogonal to the second image generation plane, thereby generating new second three-dimensional image data. On the other hand, the second image generator 15 executes the MPR process on the volume data subjected to the mask process, thereby generating new second MPR image data in the new second image generation plane. The image synthesizer 18 synthesizes the new second three-dimensional image data and the new second MPR image data, thereby generating new second synthesized image data. The display controller 17 causes the display 8 to simultaneously display a first synthesized image based on the new first synthesized image data and a second synthesized image based on the new second synthesized image data side by side.

The new first and second synthesized images displayed on the display 8 are shown in FIG. 9. The display controller 17 causes the display 8 to simultaneously display a new first synthesized image 720 generated by using the new first image generation plane and a new second synthesized image 730 generated by using the new second image generation plane side by side.

In the new first synthesized image 720, a myocardial region 722 is shown with an MPR image, and an endocardium 721 of the myocardium is shown with a three-dimensional image. Since the cardiac cavity region has been subjected to the mask process, a surface of the myocardium, which is the endocardium 721 of the myocardium in rear of the new first image generation plane taken from the view direction, is shown as a three-dimensional image, in the position of the region in which the cardiac cavity region exists in the first synthesized image 720. Moreover, in the first synthesized image 720, myocardial infarction 723 is shown on the opposite side across the cardiac cavity region taken from the view direction. This myocardial infarction 723 is shown with a three-dimensional image. Also in the second synthesized image 730, a myocardial region 732 is shown with an MPR image, and an endocardium 731 of the myocardium is shown with a three-dimensional image.

Since the cardiac cavity region has been subjected to the mask process, a surface of the myocardium, which is the endocardium 731 of the myocardium in rear of the new second image generation plane taken from the view direction, is shown as a three-dimensional image in the second synthesized image 730, in the position of the region in which the cardiac cavity region exists.

Further, in the second synthesized image 730, myocardial infarction 733 is shown as an MPR image. By the above process, the new second image generation plane is set in a position intersecting the myocardial infarction.

Thus, it becomes possible to show the myocardial infarction 733 in an MPR image representing the myocardial region 732, in the second synthesized image 730.

It becomes possible to show the myocardial infarction with a three-dimensional image in the new first synthesized image 720, and show the myocardial infarction with an MPR image in the new second synthesized image. Since it is possible to observe distribution of the myocardial infarction in the three-dimensional image and the MPR image simultaneously, assessment of the myocardial infarction is facilitated.

As described above, according to the modification 2, in order to display the myocardial infarction with an MPR image, the operator does not need to designate the view direction (angle of the image generation plane), and can generate an image in which the myocardial infarction can be easily observed in a simple operation. That is to say, without generating and displaying the first and second synthesized images while gradually rotating the first and second image generation planes, it is possible to generate an image by which the myocardial infarction is easily observed, in a simple operation. For example, since the second image generation plane intersecting with the myocardial infarction is set only by designation with the point P of the myocardial infarction 703 shown in the three-dimensional image of the first synthesized image 700 as described above, it is possible to display the cross section of the myocardial infarction in the MPR image of the second synthesized image. For example, by designating a part around the center of the myocardial infarction shown in the three-dimensional image of the first synthesized image 700, it is possible to set the second image generation plane intersecting with the part around the center of the myocardial infarction. Thus, it is possible to display the cross section in substantially center of the myocardial infarction, with the MPR image in the second synthesized image.

(Modification 3)

Figure 10:
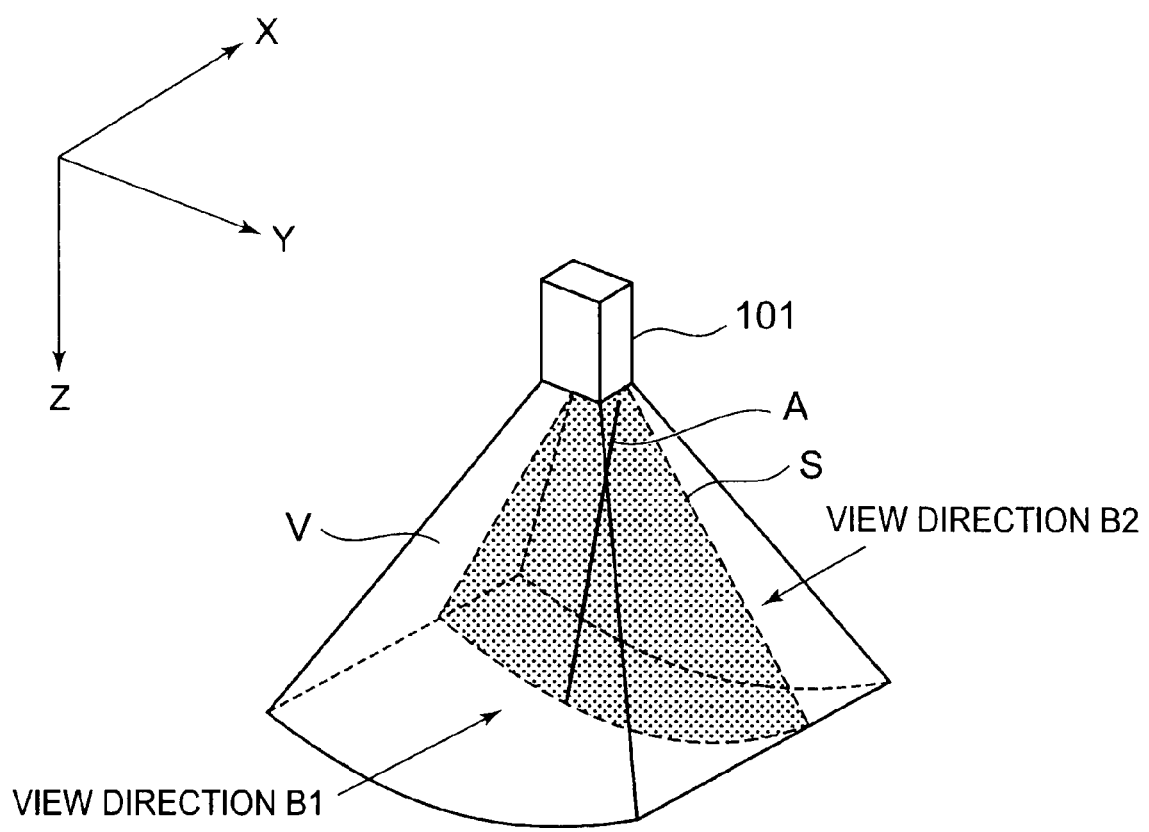
FIG. 10 is a view schematically showing a region scanned with ultrasound waves.

In a modification 3, two view directions opposite to each other are set, and image data taken from the opposite sides to each other are generated. A process according to the modification 3 will be described with reference to FIG. 10. FIG. 10 is a view schematically showing a region scanned with ultrasound waves. The first image generator 14 executes volume rendering along the view direction B1 on the volume data subjected to the mask process, thereby generating first three-dimensional image data that stereoscopically represents the tissue. The first image generator 14 generates the first three-dimensional image data based on data, excluding data included in the region in front of the image generation plane S taken from the view direction B1 and data included in the region subjected to the mask process. Consequently, three-dimensional image data will not be generated in the region up to the boundary of the region subjected to the mask process in the region in rear of the image generation plane S taken from the view direction B1 in the region subjected to the mask process.

Furthermore, the first image generator 14 executes volume rendering along the view direction B2 opposite to the view direction B1, on the volume data subjected to the mask process, thereby generating second three-dimensional image data that stereoscopically represents the tissue. The first image generator 14 generates the second three-dimensional image data based on data, excluding data included in the region in front of the image generation plane S taken from the view direction B2 and data included in the region subjected to the mask process. Consequently, three-dimensional image data will not be generated in the region up to the boundary of the region subjected to the mask process in the region in rear of the image generation plane S taken from the view direction B2 in the region having been subjected to the mask process.

On the other hand, the second image generator 15 executes the MPR process on the volume data subjected to the mask process, thereby generating MPR image data in the image generation plane S. The second image generator 15 generates the MPR image data in the image generation plane S based on data excluding data included in the region subjected to the mask process.

Then, the image synthesizer 18 synthesizes the first three-dimensional image data and the MPR image data, thereby generating first synthesized image data. Moreover, the image synthesizer 18 synthesizes the second three-dimensional image data and the MPR image data, thereby generating second synthesized image data.

The display controller 17 causes the display 8 to simultaneously display a first synthesized image based on the first synthesized image data and a second synthesized image based on the second synthesized image data.

The first and second synthesized images displayed on the display 8 are shown in FIG. 11. FIG. 11 is a view schematically showing an image generated by the medical image processing apparatus according to the embodiment of the present invention.

For example, the display controller 17 causes the display 8 to simultaneously display a first synthesized image 800 and a second synthesized image 810 side by side. The first and second synthesized images 800 and 810 are images generated by using the view directions opposite to each other.

In the first synthesized image 800, a myocardial region 802 is shown with an MPR image, and an endocardium 801 of the myocardium is shown with a three-dimensional image. Since the cardiac cavity region has been subjected to the mask process, a surface of the myocardium, which is the endocardium 801 of the myocardium in rear of the image generation plane S taken from the view direction B1, is shown as a three-dimensional image in the position of a region in which the cardiac cavity region exists, in the first synthesized image 800. In the first synthesized image 800, myocardial infarction 803 is shown on the opposite side across the cardiac cavity region taken from the view direction B1. This myocardial infarction 803 is shown with a three-dimensional image.

Further, in the second synthesized image 810, a myocardial region 812 is shown with an MPR image, and an endocardium 811 of the myocardium is shown with a three-dimensional image. Since the cardiac cavity region has been subjected to the mask process, a surface of the myocardium, which is the endocardium 811 of the myocardium in rear of the image generation pane S taken from the view direction B2 (a direction opposite to the view direction B1), is shown as a three-dimensional image in the position of the region in which the cardiac cavity region exists in the second synthesized image 810.

As described above, the view directions are opposite to each other in the first synthesized image 800 and the second synthesized image 810.

Therefore, with reference to the view direction B1 in the first synthesized image 800, the endocardium 811 of the myocardium in front of the image generation plane S taken from the view direction B1 is shown in the second synthesized image 810. That is to say, the endocardium 811 of the myocardium shown in the second synthesized image 810 represents the endocardium of the myocardium in front of the image generation plane S taken from the view direction B1. Thus, the endocardium of the myocardium in front of the image generation plane S taken from the view direction B1, which is not shown in the first synthesized image 800, is shown in the second synthesized image 810. Similarly, the endocardium 801 of the myocardium in front of the image generation plane S taken from the view direction B2 is shown in the first synthesized image 810. That is to say, the endocardium 801 of the myocardium shown in the first synthesized image 800 represents the endocardium of the myocardium in front of the image generation plane S taken from the view direction B2. Thus, the endocardium of the myocardium in front of the image generation plane S taken from the view direction B2, which is not shown in the second synthesized image 810, is shown in the first synthesized image 800.

Then, when the operator changes the view direction B1 (the angle of the image generation plane) by using the input part 7, the first image generator 14 generates first three-dimensional image data by using the changed view direction B1, and generates second three-dimensional image data by using the view direction B2 opposite to the changed view direction B1.

As described above, by generating and displaying the first and second synthesized images 800 and 810 in which the view directions are opposite to each other, it is possible to reduce the work required for observing the whole inside of the myocardial region. For example, it is possible to observe the whole inside of the myocardial region even if the amount of rotation of the image generation plane is decreased to half of that in the case of generating and displaying a synthesized image by using one view direction. For example, in the case of generating and displaying a synthesized image by using one view direction, for observation of the whole inside of the myocardial region, it is necessary to gradually rotate the image generation plane 360 degrees to generate and display a synthesized image in the image generation plane at each angle. On the other hand, since view directions opposite to each other are set and synthesized images by using the respective view directions are generated and displayed in the modification 3, it is possible to display the whole inside of the myocardial region only by rotating the image generation plane 180 degrees.

Further, instead of simultaneously displaying the first and second synthesized images 800 and 810, the display controller 17 may switch to display each of the images. For example, when the operator gives an instruction to switch the images by using the input part 7, the display controller 17 switches the first and second synthesized images 800 and 810 in response to the switching instruction and causes the display 8 to display.

(Modification 4)

In a modification 4, a three-dimensional image that stereoscopically shows the surface of the cardiac cavity region is generated and displayed.

Upon reception of the volume data in which the cardiac cavity region has been subjected to the mask process, the image generator 13 executes volume rendering on the volume data, thereby generating three-dimensional image data that stereoscopically represents the surface of the mask region.

That is to say, the image generator 13 generates three-dimensional image data that stereoscopically represents the surface of the cardiac cavity region. Moreover, the image generator 13 receives the coordinate information of the image generation plane S from the image generation plane determining part 12, and generates image data schematically representing a frame shape as the shape of the image generation plane S. The image generator 13 synthesizes the image data representing the frame shape with the three-dimensional image data representing the surface of the cardiac cavity region, thereby generating cardiac cavity image data. The image generator 13 outputs the cardiac cavity image data to the display controller 17. The display controller 17 causes the display 8 to simultaneously display a synthesized image based on the synthesized image data generated by the image synthesizer 18 and a cardiac cavity image based on the cardiac cavity image data side by side.

Figure 12:
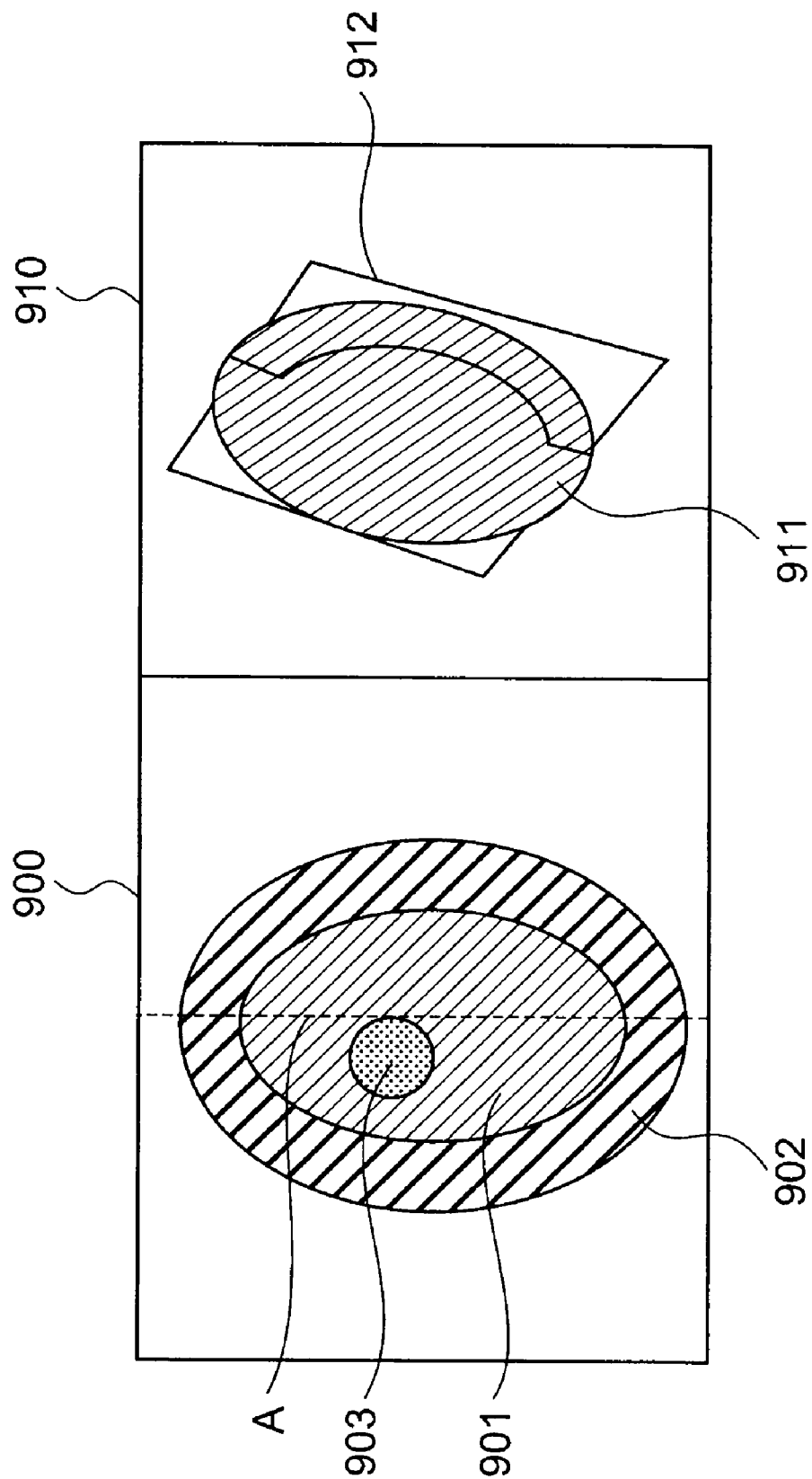
FIG. 12 is a view schematically showing a synthesized image and a cardiac cavity image.

An example of the cardiac cavity image is shown in FIG. 12. FIG. 12 is a view schematically showing the synthesized image and the cardiac cavity image. The display controller 17 causes the display 8 to simultaneously display a synthesized image 900 generated by the image synthesizer 18 and a cardiac cavity image 910 generated by the image generator 13 side by side.

The synthesized image 900 is an image generated by using the view direction B and the image generation plane S as in the above embodiment. In the synthesized image 900, a myocardial region 902 is shown with an MPR image, and an endocardium 901 of the myocardium is shown with a three-dimensional image. Since the cardiac cavity region has been subjected to the mask process, a surface of the myocardium, which is the endocardium 901 of the myocardium in rear of the image generation plane S taken from the view direction B, is shown as a three-dimensional image in the position of the region in which the cardiac cavity region exists in the synthesized image 900.

Moreover, in the synthesized image 900, myocardial infarction 903 is shown on the opposite side across the cardiac cavity region taken from the view direction B. The myocardial infarction 903 is shown with a three-dimensional image.

On the other hand, in a cardiac cavity image 910, the surface of a mask region 911 is stereoscopically shown. That is, in the cardiac cavity image 910, the surface of the cardiac cavity region is stereoscopically shown.

Furthermore, since image data representing a frame-shaped image generation plane S is included in the cardiac cavity image data, a frame 912 representing the image generation plane S is shown in the cardiac cavity image 910 displayed on the display 8. The display controller 17 may cause the display 8 to display the cardiac cavity image 910 translucently. Thus, the surface of the cardiac cavity region is displayed translucently.

By observing the cardiac cavity image 910, the operator can easily grasp the position of the image generation plane S with respect to the cardiac cavity region. Thus, the operator can easily set the image generation plane S in a desired position while observing the cardiac cavity image 910.

Also in the case of setting a plurality of image generation planes to generate and display a plurality of synthesized images as in the modification 1, a cardiac cavity image may be generated and displayed. As an example, a case of generating two synthesized image data as in the modification 1 will be described. The image generator 13, as described above, executes volume rendering on volume data in which a cardiac cavity region has been subjected to the mask process, thereby generating three-dimensional image data that stereoscopically represents the surface of a mask region (a cardiac cavity region). Furthermore, the image generator 13 receives coordinate information of a first image generation plane and coordinate information of a second image generation plane that is different from the first image generation plane, from the image generation plane determining part 12. The image generator 13 generates image data that represents a frame shape as the shape of the first image generation plane and image data that represents a frame shape as the shape of the second image generation plane. The image generator 13 synthesizes the image data representing the first image generation plane and the image data representing the second image generation plane with the three-dimensional image data representing the surface of the cardiac cavity region, thereby generating cardiac cavity image data. The display controller 17 causes the display 8 to simultaneously display a first synthesized image based on first synthesized image data, a second synthesized image based on second synthesized image data, and a cardiac cavity image based on the cardiac cavity image data side by side.

Figure 13:
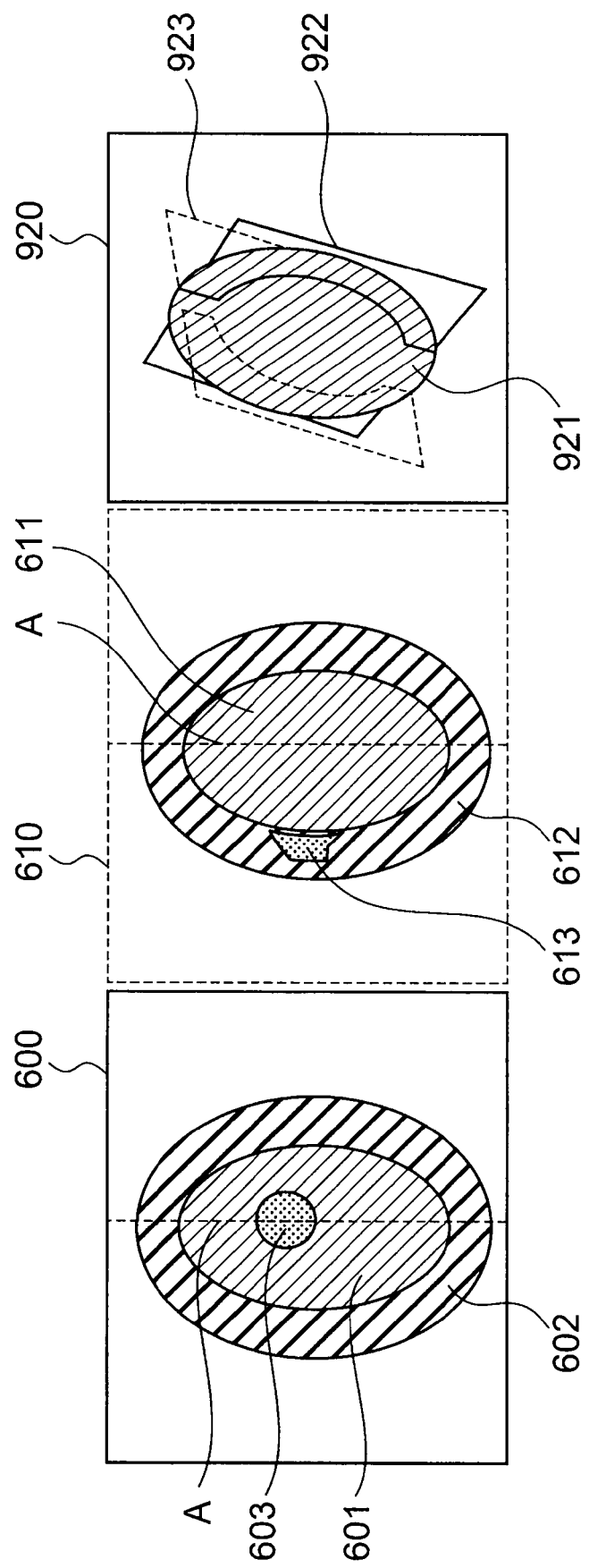
FIG. 13 is a view schematically showing a synthesized image and a cardiac cavity image.

An example of the cardiac cavity image is shown in FIG. 13. FIG. 13 is a view schematically showing a synthesized image and a cardiac cavity image.

The display controller 17 causes the display 8 to simultaneously display a first synthesized image 600, a second synthesized image 610, and a cardiac cavity image 920 side by side. The first synthesized image 600 and the second synthesized image 610 are images generated by the image generator 18. For example, as in the modification 1, the first synthesized image 600 and the second synthesized image 610 represent images in mutually orthogonal planes.

Further, in the cardiac cavity image 920, the surface of a mask region 921 (a cardiac cavity region) is stereoscopically shown. Furthermore, since image data representing a frame shape as the shape of a first image generation plane and image data representing a frame shape as the shape of a second image generation plane are included in the cardiac cavity image data, a frame 922 representing the first image generation plane and a frame 923 representing the second image generation plane are shown in the cardiac cavity image 920 displayed on the display 8. The display controller 17 may cause the display 8 to display the cardiac cavity image 920 translucently.

Furthermore, in the case of displaying a plurality of synthesized images and displaying a plurality of frames in a cardiac cavity image, the display controller 17 may cause the display 8 to display the frames in different display modes from each other. In the example shown in FIG. 13, the display controller 17 causes the display 8 to display the frame 922 representing the first image generation plane and the frame 923 representing the second image generation plane in different display modes from each other.

For example, the display controller 17 causes the display 8 to display the frames in different colors, line types (solid line, broken line), etc. For example, the display controller 17 causes the display 8 to display the frame 922 that represents the first image generation plane by a solid line and the frame 923 that represents the second image generation plane by a broken line.

Alternatively, the display controller 17 may cause the display 8 to display the frame 922 that represents the first image generation plane and the frame 923 that represents the second image generation plane in different colors.

Furthermore, the display controller 17 may cause the display 8 to display the rim of the display section of a synthesized image in the same display mode as the frame representing an image generation plane in which the synthesized image has been generated. Consequently, the display mode of the rim of the display section of the synthesized image and the display mode of the frame representing the image generation plane in which the synthesized image has been generated are associated with each other. The display controller 17 causes the display 8 to display so that the display mode of the rim of the display section of the first synthesized image generated by using the first image generation plane is the same as the display mode of the frame 922 representing the first image generation plane. For example, the display controller 17 causes the display 8 to display the rim of the display section and the frame with the same color, line type (solid line, broken line), etc. For example, as shown in FIG. 13, the display controller 17 causes the display 8 to display the frame 922 representing the first image generation plane by a solid line, and display the rim of the display section of the first synthesized image 600 generated by using the first image generation plane by a solid line. On the other hand, the display controller 17 causes to display the frame 923 representing the second image generation plane by a broken line, and display the rim of the display section of the second synthesized image 610 generated by using the second image generation plane by a broken line. Alternatively, the display controller 17 may cause the display 8 to display the frame 922 and the rim of the display section of the first synthesized image in one color, and display the frame 923 and the rim of the display section of the second synthesized image 610 in another color.

Then, when the operator changes the view direction (the angle of the image generation plane) by using the input part 7, in response to the change, the positions of the frames 922 and 923 representing the image generation planes are changed, and the frames are displayed on the display 8.

As described above, by displaying the rim of the display section and the frame in the same display mode, the operator can easily grasp the association between the synthesized image and the image generation plane (frame). That is, the operator can easily grasp what synthesized image is generated by using each of the image generation planes.

The cardiac cavity region specifying part 4, the rotation axis specifying part 5, the main controller 6 and the image processor 10 may be each composed of a not-shown CPU (Central Processing Unit) and a not-shown storage device such as a ROM (Read Only Memory), a RAM (Random Access Memory) and an HDD (Hard Disk Drive). The storage device stores: a cardiac cavity region specifying program for executing the function of the cardiac cavity specifying part 4; a rotation axis specifying program for executing the function of the rotation axis specifying part 5; a control program for executing the function of the main controller 6; and an image processing program for executing the function of the image processor 10.

Moreover, the image processing program includes: an image generation control program for executing the function of the image generation controller 11; an image generation plane determining program for executing the function of the image generation plane determining part 12; an image generation program for executing the function of the image generator 13; a mask region changing program for executing the function of the mask region changer 16; and a display control program for executing the function of the display controller 17. Moreover, the image generation program includes a first image generation program for executing the function of the first image generator 14, and a second image generation program for executing the function of the second image generator 15. Moreover, the display control program includes an image synthesizing program for executing the function of the image synthesizer 18. Through execution of the respective programs by the CPU, the functions of the respective parts are executed.

Further, an imaging apparatus provided with the medical image processing apparatus 1 and the ultrasound imaging apparatus 100 can also produce the same actions and effects as the medical image processing apparatus 1 according to this embodiment. The medical image processing apparatus 1 and the ultrasound imaging apparatus 100 compose an example of an "ultrasound imaging apparatus" of the present invention.

Further, the medical image processing apparatus 1 according to this embodiment may generate synthesized image data based on volume data acquired by a medical image capturing apparatus other than the ultrasound imaging apparatus 100. For example, the medical image processing apparatus 1 may generate synthesized image data based on volume data of a subject acquired by an X-ray CT apparatus. The X-ray CT apparatus is provided with an X-ray tube that radiates an X-ray, an X-ray detector placed opposite to the X-ray tube across a subject, and a reconstruction processor. Then, the X-ray CT apparatus rotates the X-ray tube and the X-ray detector around the subject while radiating an X-ray from the X-ray tube, thereby collecting X-ray projection data. The reconstruction processor reconstructs the collected X-ray projection data by a known reconstruction method, thereby generating volume data representing the subject. The medial image processing apparatus 1 receives the volume data acquired by the X-ray CT apparatus, and generates synthesized image data based on the volume data. Moreover, an apparatus provided with the medical image processing apparatus 1 and the X-ray CT apparatus can also produce the same actions and effects as the medical image processing apparatus 1 according to this embodiment. The medical image processing apparatus 1 and the X-ray CT apparatus compose an example of an "X-ray CT apparatus" of the present invention.

What is claimed is:

1. A medical image processing apparatus, comprising:
a cardiac cavity region specifying part configured to receive volume data representing a heart and specify a position of a cardiac cavity region represented in the volume data;
an axis setting part configured to set an axis intersecting the cardiac cavity region;
an image generation plane setting part configured to set an image generation plane including the axis in the volume data;
a first image generator configured to, based on the volume data, generate three-dimensional image data that stereoscopically represents a boundary of the cardiac cavity region, which is a boundary of one of regions of the cardiac cavity region divided by the image generation plane;
a second image generator configured to, based on data excluding data included in the cardiac cavity region of the volume data, generate two-dimensional image data that two-dimensionally represents a region in the image generation plane; and
a display controller configured to generate new synthesized image data by synthesizing the three-dimensional image data and the two-dimensional image data, and cause a display to display a synthesized image based on the new synthesized image data,
wherein the cardiac cavity region specifying part is configured to define a mask region about the cardiac cavity region; and
the second image generator is configured to generate a two dimensional image using the volume data excluding that of the mask region.

2. The medical image processing apparatus according to claim 1, wherein the first image generator executes a rendering process with a direction orthogonal to the image generation plane as a view direction, on the data excluding the data included in the cardiac cavity region of the volume data, thereby generating the three-dimensional image data that stereoscopically represents the boundary of the one region excluding the cardiac cavity region.

3. The medical image processing apparatus according to claim 2, wherein the first image generator further executes the rendering process on data excluding data included in a dilated region larger than the cardiac cavity region of the volume data, thereby generating three-dimensional image data that stereoscopically represents a region excluding the dilated region.

4. The medical image processing apparatus according to claim 2, wherein:
the first image generator sets a first view direction orthogonal to the image generation plane, and a second view direction opposite to the first view direction, generates first three-dimensional image data by executing the rendering process in the first view direction on the data excluding the data included in the cardiac cavity region of the volume data, and generates second three-dimensional image data by executing the rendering process in the second view direction on the data excluding the data included in the cardiac cavity region of the volume data; and
the display controller generates first synthesized image data by synthesizing the first three-dimensional image data and the two-dimensional image data, generates second synthesized image data by synthesizing the second three-dimensional image data and the two-dimensional image data, and causes the display to display a first synthesized image based on the first synthesized image data and a second synthesized image based on the second synthesized image data.

5. The medical image processing apparatus according to claim 1, wherein:
the image generation plane setting part receives designation of an angle of the image generation plane, rotates the image generation plane around the axis by the designated angle, and sets a new image generation plane in place of the image generation plane;
the first image generator generates new three-dimensional image data by using the new image generation plane;
the second image generator generates new two-dimensional image data in the new image generation plane; and
the display controller generates new synthesized image data by synthesizing the new three-dimensional image data and the new two-dimensional image data, and causes the display to display a synthesized image based on the new synthesized image data.

6. The medical image processing apparatus according to claim 1, wherein:
the image generation plane setting part sets the image generation plane, and a second image generation plane that includes the axis and intersects the image generation plane;
the first image generator generates first three-dimensional image data by using the image generation plane, and second three-dimensional image data by using the second image generation plane;
the second image generator generates first two-dimensional image data in the image generation plane, and second two-dimensional image data in the second image generation plane; and
the display controller generates first synthesized image data by synthesizing the first three-dimensional image data and the first two-dimensional image data, generates second synthesized image data by synthesizing the second three-dimensional image data and the second two-dimensional image data, and causes the display to display a first synthesized image based on the first synthesized image data and a second synthesized image based on the second synthesized image data.

7. The medical image processing apparatus according to claim 6, wherein the image generation plane setting part sets a plane that includes the axis and that is orthogonal to the image generation plane, as the second image generation plane.

8. The medical image processing apparatus according to claim 1, wherein:
upon reception of designation of an optional point on the synthesized image displayed on the display, the image generation plane setting part obtains a line that passes through the designated point and that is orthogonal to the image generation plane, obtains an intersection of the line and the boundary of the cardiac cavity region, and sets a plane including the intersection and the axis as a new image generation plane in place of the image generation plane;
the first image generator generates new three-dimensional image data by using the new image generation plane;
the second image generator generates new two-dimensional image data in the new image generation plane; and
the display controller generates new synthesized image data by synthesizing the new three-dimensional image data and the new two-dimensional image data, and causes the display to display a synthesized image based on the new synthesized image data.

9. The medical image processing apparatus according to claim 8, wherein:
the image generation plane setting part sets the new image generation plane, and another image generation plane that includes the axis and that is orthogonal to the new image generation plane;
the first image generator generates the new three-dimensional image data by using the new image generation plane, and generates another three-dimensional image data by using the other image generation plane;
the second image generator generates the new two-dimensional image data in the new image generation plane, and generates another two-dimensional image data in the other image generation plane; and
the display controller generates the new synthesized image data by synthesizing the new three-dimensional image data and the new two-dimensional image data, generates another synthesized image data by synthesizing the other three-dimensional image data and the other two-dimensional image data, and causes the display to display the synthesized image based on the new synthesized image data and another synthesized image based on the other synthesized image data.

10. The medical image processing apparatus according to claim 1, further comprising:
an image generator configured to generate three-dimensional image data that stereoscopically represents a surface of the cardiac cavity region based on the volume data, generate image data that represents the image generation plane in a frame shape, and generate cardiac cavity image data by synthesizing the three-dimensional image data representing the cardiac cavity region and the image data representing the image generation plane, wherein:
the display controller further causes the display to display a cardiac cavity image based on the cardiac cavity image data.

11. An ultrasound imaging apparatus, comprising:
an imaging part configured to, with a heart of a subject as an imaging target, transmit ultrasound waves to the subject and acquire volume data representing the heart of the subject based on reflected waves from the subject;
a cardiac cavity region specifying part configured to specify a position of a cardiac cavity region represented in the volume data;
an axis setting part configured to set an axis intersecting the cardiac cavity region;
an image generation plane setting part configured to set an image generation plane including the axis in the volume data;
a first image generator configured to generate, based on the volume data, three-dimensional image data that stereoscopically represents a boundary of the cardiac cavity region, which is a boundary of one of regions of the cardiac cavity region divided by the image generation plane;
a second image generator configured to generate two-dimensional image data that two-dimensionally represents a region in the image generation plane based on data excluding data included in the cardiac cavity region of the volume data; and
a display controller configured to generate new synthesized image data by synthesizing the three-dimensional image data and the two-dimensional image data, and cause a display to display a synthesized image based on the new synthesized image data,
wherein the cardiac cavity region specifying part is configured to define a mask region about the cardiac cavity region; and
the second image generator is configured to generate a two dimensional image using the volume data excluding that of the mask region.

12. An X-ray CT apparatus, comprising:
an imaging part configured to, with a heart of a subject as an imaging target, irradiate the subject with an X-ray and acquire volume data representing the heart of the subject based on the X-ray transmitted through the subject;
a cardiac cavity region specifying part configured to specify a position of a cardiac cavity region represented in the volume data;
an axis setting part configured to set an axis intersecting the cardiac cavity region;
an image generation plane setting part configured to set an image generation plane including the axis in the volume data;
a first image generator configured to generate three-dimensional image data that stereoscopically represents a boundary of the cardiac cavity region, which is a boundary of one of regions of the cardiac cavity region divided by the image generation plane;
a second image generator configured to generate two-dimensional image data that two-dimensionally represents a region in the image generation plane based on data excluding data included in the cardiac cavity region of the volume data; and
a display controller configured to generate new synthesized image data by synthesizing the three-dimensional image data and the two-dimensional image data, and cause a display to display a synthesized image based on the new synthesized image data,
wherein the cardiac cavity region specifying part is configured to define a mask region about the cardiac cavity region; and
the second image generator is configured to generate a two dimensional image using the volume data excluding that of the mask region.

13. A method of processing a medical image, comprising:
receiving volume data that represents a heart and specifying a position of a cardiac cavity region represented in the volume data;
setting an axis that intersects the cardiac cavity region;
setting an image generation plane that includes the axis in the volume data;
generating three-dimensional image data that stereoscopically represents a boundary of the cardiac cavity region, which is a boundary of one of regions of the cardiac cavity region divided by the image generation plane, based on the volume data;
generating two-dimensional image data that two-dimensionally represents a region in the image generation plane based on data excluding data included in the cardiac cavity region of the volume data;
generating synthesized image data by synthesizing the three-dimensional image data and the two-dimensional image data, and displaying a synthesized image based on the synthesized image data;
defining a mask region about the cardiac cavity region; and
generating a two dimensional image using the volume data excluding that of the mask region.

14. The method of processing a medical image according to claim 13, wherein, with a direction orthogonal to the image generation plane as a view direction, a rendering process is executed on the data excluding the data included in the cardiac cavity region of the volume data, and the three-dimensional image data that stereoscopically represents the boundary of the one region excluding the cardiac cavity region is thereby generated.

15. The method of processing a medical image according to claim 14, wherein the rendering process is executed on data excluding data included in a dilated region larger than the cardiac cavity region of the volume data, and three-dimensional image data that stereoscopically represents a region excluding the dilated region is thereby generated.

16. The method of processing a medical image according to claim 13, wherein:
   designation of an angle of the image generation plane is received, the image generation plane is rotated around the axis by the designated angle, and a new image generation plane in place of the image generation plane is set;
   new three-dimensional image data is generated by using the new image generation plane;
   new two-dimensional image data is generated in the new image generation plane; and
   new synthesized image data is generated by synthesizing the new three-dimensional image data and the new two-dimensional image data, and a synthesized image based on the new synthesized image data is displayed.

17. The method of processing a medical image according to claim 13, wherein:
   the image generation plane and a second image generation plane that includes the axis and intersects the image generation plane are set;
   first three-dimensional image data is generated by using the image generation plane and second three-dimensional image data is generated by using the second image generation plane;
   first two-dimensional image data in the image generation plane is generated, and second two-dimensional image data in the second image generation plane is generated; and
   first synthesized image data is generated by synthesizing the first three-dimensional image data and the first two-dimensional image data, second synthesized image data is generated by synthesizing the second three-dimensional image data and the second two-dimensional image data, and a first synthesized image based on the first synthesized image data and a second synthesized image based on the second synthesized image data are displayed.

18. The method of processing a medical image according to claim 17, wherein a plane that includes the axis and that is orthogonal to the image generation plane is set as the second image generation plane.

19. The method of processing a medical image according to claim 13, wherein:
   when designation of an optional point on the synthesized image displayed on the display is received, a line that passes through the designated point and that is orthogonal to the image generation plane is obtained, an intersection of the line and the boundary of the cardiac cavity region is obtained, and a plane including the intersection and the axis is set as a new image generation plane in place of the image generation plane;
   new three-dimensional image data is generated by using the new image generation plane;
   new two-dimensional image data is generated in the new image generation plane; and
   new synthesized image data is generated by synthesizing the new three-dimensional image data and the new two-dimensional image data, and a synthesized image based on the new synthesized image data is displayed.

20. The method of processing a medical image according to claim 19, wherein:
   the new image generation plane and another image generation plane that includes the axis and that is orthogonal to the new image generation plane are set;
   the new three-dimensional image data is generated by using the new image generation plane, and another three-dimensional image data is generated by using the other image generation plane;
   the new two-dimensional image data is generated in the new image generation plane, and another two-dimensional image data is generated in the other image generation plane; and
   the new synthesized image data is generated by synthesizing the new three-dimensional image data and the new two-dimensional image data, another synthesized image data is generated by synthesizing the other three-dimensional image data and the other two-dimensional image data, and a synthesized image based on the new synthesized image data and another synthesized image based on the other synthesized image data are displayed.

* * * * *